US011278687B2

(12) United States Patent
Sudlow et al.

(10) Patent No.: US 11,278,687 B2
(45) Date of Patent: Mar. 22, 2022

(54) AEROSOL DELIVERY SYSTEM WITH AN ACTIVATION SURFACE

(71) Applicant: Nerudia Limited, Liverpool (GB)

(72) Inventors: Tom Sudlow, Liverpool (GB); Chris Lord, Liverpool (GB); David Jones, Liverpool (GB); Edward Ross Shenton, Liverpool (GB)

(73) Assignee: NERUDIA LIMITED, Liverpool (GB)

( * ) Notice: Subject to any disclaimer, the term of this patent is extended or adjusted under 35 U.S.C. 154(b) by 146 days.

(21) Appl. No.: 16/608,750

(22) PCT Filed: Apr. 24, 2018

(86) PCT No.: PCT/EP2018/060500
§ 371 (c)(1),
(2) Date: Oct. 25, 2019

(87) PCT Pub. No.: WO2018/197511
PCT Pub. Date: Nov. 1, 2018

(65) Prior Publication Data
US 2020/0187561 A1   Jun. 18, 2020

(30) Foreign Application Priority Data

Apr. 25, 2017   (GB) .................................. 1706593
Feb. 22, 2018   (GB) .................................. 1802836
Feb. 22, 2018   (GB) .................................. 1802837

(51) Int. Cl.
*A24F 40/48*   (2020.01)
*A61M 15/06*   (2006.01)
(Continued)

(52) U.S. Cl.
CPC ............. *A61M 15/06* (2013.01); *A24F 40/42* (2020.01); *A24F 40/44* (2020.01); *A24F 40/46* (2020.01);
(Continued)

(58) Field of Classification Search
CPC .......... A24F 40/10; A24F 40/40; A24F 40/46; A24F 40/48; A61M 11/04; A61M 15/06
(Continued)

(56) References Cited

U.S. PATENT DOCUMENTS 5,766,709 A * 6/1998 Geddes .................... B65D 3/14
220/902
2008/0245305 A1   10/2008 Ikarashi et al.
(Continued)

FOREIGN PATENT DOCUMENTS

CN   103876289 A   6/2014
CN   203662018 U   6/2014
(Continued)

OTHER PUBLICATIONS

PCT International Search Report for PCT/EP2018/060500 dated Jun. 25, 2018; 12 Pages.
(Continued)

*Primary Examiner* — Hae Moon Hyeon
(74) *Attorney, Agent, or Firm* — Brandon V. Zuniga; James R. Gourley; Carstens & Cahoon, LLP

(57) ABSTRACT

There is disclosed a fluid-transfer article which is suitable for use as part of an aerosol-generating system. The fluid-transfer-article comprises a first region for holding an aerosol precursor and for transferring said aerosol precursor to an activation surface of a second region of said article. The activation surface is disposed at an end of said article configured for thermal interaction with a heater of an aerosol-generation apparatus. At least the second region of the fluid-transfer article is formed from a polymeric wicking material.

30 Claims, 17 Drawing Sheets

(51) Int. Cl.
  *A24F 40/44* (2020.01)
  *A24F 40/42* (2020.01)
  *A61M 11/04* (2006.01)
  *A61M 15/00* (2006.01)
  *A24F 40/46* (2020.01)
  *H05B 3/20* (2006.01)
  *A24F 40/10* (2020.01)
(52) U.S. Cl.
  CPC ........... *A24F 40/48* (2020.01); *A61M 11/042* (2014.02); *A61M 15/009* (2013.01); *H05B 3/20* (2013.01); *A24F 40/10* (2020.01); *A61M 2205/0233* (2013.01); *H05B 2203/002* (2013.01); *H05B 2203/021* (2013.01)
(58) Field of Classification Search
  USPC .................................................. 131/328, 329
  See application file for complete search history.

(56) References Cited

U.S. PATENT DOCUMENTS

| | | |
|---|---|---|
| 2010/0181387 A1 | 7/2010 | Zaffaroni et al. |
| 2011/0023899 A1 | 2/2011 | Strickland et al. |
| 2011/0083676 A1 | 4/2011 | Karles et al. |
| 2013/0228191 A1 | 9/2013 | Newton |
| 2015/0059780 A1 | 3/2015 | Davis et al. |
| 2015/0114409 A1* | 4/2015 | Brammer ............ A61M 11/007 131/329 |
| 2015/0208728 A1 | 7/2015 | Lord |
| 2015/0245669 A1* | 9/2015 | Cadieux ................ A24F 40/50 131/329 |
| 2015/0257447 A1 | 9/2015 | Sullivan |
| 2015/0367016 A1 | 12/2015 | Gruenbacher et al. |
| 2016/0143358 A1 | 5/2016 | Zhu |
| 2016/0330999 A1 | 11/2016 | Cameron |
| 2017/0020193 A1 | 1/2017 | Davis et al. |
| 2017/0042243 A1 | 2/2017 | Plojoux et al. |
| 2017/0049153 A1 | 2/2017 | Guo et al. |
| 2017/0181472 A1 | 6/2017 | Batista et al. |
| 2017/0188626 A1 | 7/2017 | Davis et al. |
| 2017/0196269 A1 | 7/2017 | Bernauer et al. |
| 2018/0007741 A1 | 1/2018 | Metz et al. |
| 2018/0035721 A1 | 2/2018 | Cyphert et al. |
| 2018/0042301 A1 | 2/2018 | Rostami |
| 2019/0046741 A1* | 2/2019 | Lord ...................... A24F 40/42 |
| 2021/0100286 A1* | 4/2021 | Sudlow ............... A61M 15/009 |

FOREIGN PATENT DOCUMENTS

| | | |
|---|---|---|
| CN | 204796739 U | 11/2015 |
| CN | 205180364 U | 4/2016 |
| CN | 205250356 U | 5/2016 |
| CN | 106490686 A | 3/2017 |
| EP | 3135135 A1 | 3/2017 |
| EP | 3332657 A1 | 6/2018 |
| GB | 2504076 A | 1/2014 |
| WO | 2011/045672 | 4/2011 |
| WO | 2015077645 A1 | 5/2015 |
| WO | 2015101479 A1 | 7/2015 |
| WO | 2015/117704 | 8/2015 |
| WO | 2015114325 A1 | 8/2015 |
| WO | 2015117705 A3 | 10/2015 |
| WO | 2016/061166 | 4/2016 |
| WO | 2016/079152 | 5/2016 |
| WO | 2016/079155 | 5/2016 |
| WO | 2016096728 A1 | 6/2016 |
| WO | 2016/135224 | 9/2016 |
| WO | 2016145072 A1 | 9/2016 |
| WO | 2016/156217 | 10/2016 |
| WO | 2016154792 A1 | 10/2016 |
| WO | 2016/174179 | 11/2016 |
| WO | 2017001818 A1 | 1/2017 |
| WO | 2017005471 A1 | 1/2017 |
| WO | 2017093535 A1 | 6/2017 |
| WO | 2017118927 A1 | 7/2017 |
| WO | 2017/191176 | 11/2017 |
| WO | 2018007625 A1 | 1/2018 |

OTHER PUBLICATIONS

GB Search Report for GB1706593.9 dated Jul. 17, 2018; 9 Pages.
GB Search Report for GB1802836.5 dated Jul. 18, 2018; 7 Pages.
GB Search Report for GB1802837.3 dated Aug. 15, 2018; 6 Pages.

* cited by examiner

AEROSOL DELIVERY SYSTEM WITH AN ACTIVATION SURFACE

CROSS-REFERENCE TO RELATED APPLICATIONS

This application is a U.S. 371 Application from PCT/EP2018/060500 Apr. 24, 2018, which claims priority from GB1706593.9 filed 25 Apr. 2017; GB1802836.5 filed 22 Feb. 2018; and from GB1802837.3 filed 22 Feb. 2018, the contents and elements of which are herein incorporated by reference for all purposes.

STATEMENT REGARDING FEDERALLY SPONSORED RESEARCH OR DEVELOPMENTS

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

Field of the Invention

The present invention relates to an aerosol delivery system, a carrier for an aerosol precursor and a fluid-transfer article for an aerosol delivery system. In particular, the present invention relates to an aerosol delivery system comprising a heater configured to heat an aerosol precursor to generate an aerosolised composition for inhalation by a user.

DESCRIPTION OF RELATED ART INCLUDING INFORMATION DISCLOSED UNDER 37 CFR 1.97 AND 1.98

Pharmaceutical medicament, physiologically active substances and flavourings for example may be delivered to the human body by inhalation through the mouth and/or nose. Such material or substances may be delivered directly to the mucosa or mucous membrane lining the nasal and oral passages and/or the pulmonary system. For example, nicotine is consumed for therapeutic or recreational purposes and may be delivered to the body in a number of ways. Nicotine replacement therapies are aimed at people who wish to stop smoking and overcome their dependence on nicotine. Nicotine is delivered to the body in the form of aerosol delivery devices and systems, also known as smoking-substitute devices or nicotine delivery devices. Such devices may be non-powered or powered.

Devices or systems that are non-powered may comprise nicotine replacement therapy devices such as "inhalators", e.g. Nicorette® Inhalator. These generally have the appearance of a plastic cigarette and are used by people who crave the behaviour associated with consumption of combustible tobacco—the so-called hand-to-mouth aspect—of smoking tobacco. Inhalators generally allow nicotine-containing aerosol to be inhaled through an elongate tube in which a container containing a nicotine carrier, for example, a substrate, is located. An air stream caused by suction through the tube by the user carries nicotine vapours into the lungs of the user to satisfy a nicotine craving. The container may comprise a replaceable cartridge, which includes a cartridge housing and a passageway in the housing in which a nicotine reservoir is located. The reservoir holds a measured amount of nicotine in the form of the nicotine carrier. The measured amount of nicotine is an amount suitable for delivering a specific number of "doses". The form of the nicotine carrier is such as to allow nicotine vapour to be released into a fluid stream passing around or through the reservoir. This process is known as aerosolization and or atomization. Aerosolization is the process or act of converting a physical substance into the form of particles small and light enough to be carried on the air i.e. into an aerosol. Atomization is the process or act of separating or reducing a physical substance into fine particles and may include the generation of aerosols. The passageway generally has an opening at each end for communication with the exterior of the housing and for allowing the fluid stream through the passageway. A nicotine-impermeable barrier seals the reservoir from atmosphere. The barrier includes passageway barrier portions for sealing the passageway on both sides of the reservoir. These barrier portions are frangible so as to be penetrable for opening the passageway to atmosphere.

A device or a system that is powered can fall into two sub-categories. In both subcategories, such devices or systems may comprise electronic devices or systems that permit a user to simulate the act of smoking by producing an aerosol mist or vapour that is drawn into the lungs through the mouth and then exhaled. The electronic devices or systems typically cause the vaporization of a liquid containing nicotine and entrainment of the vapour into an airstream. Vaporization of an element or compound is a phase transition from the liquid phase to vapour i.e. evaporation or boiling. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

A person of ordinary skill in the art will appreciate that devices or systems of the second, powered category as used herein include, but are not limited to, electronic nicotine delivery systems, electronic cigarettes, e-cigarettes, e-cigs, vaping cigarettes, pipes, cigars, cigarillos, vaporizers and devices of a similar nature that function to produce an aerosol mist or vapour that is inhaled by a user. Such nicotine delivery devices or systems of the second category incorporate a liquid reservoir element generally including a vaporizer or misting element such as a heating element or other suitable element, and are known, inter alia, as atomizers, cartomizers, or clearomizers. Some electronic cigarettes are disposable; others are reusable, with replaceable and refillable parts.

Aerosol delivery devices or systems in a first sub-category of the second, powered category generally use heat and/or ultrasonic agitation to vaporize a solution comprising nicotine and/or other flavouring, propylene glycol and/or glycerine-based base into an aerosol mist of vapour for inhalation.

Aerosol delivery devices or systems in a second sub-category of the second, powered category may typically comprise devices or systems in which tobacco is heated rather than combusted. During use, volatile compounds may be released from the tobacco by heat transfer from the heat source and entrained in air drawn through the aerosol delivery device or system. Direct contact between a heat source of the aerosol delivery device or system and the tobacco heats the tobacco to form an aerosol. As the aerosol containing the released compounds passes through the device, it cools and condenses to form an aerosol for inhalation by the user. In such devices or systems, heating, as opposed to burning, the tobacco may reduce the odour that can arise through combustion and pyrolytic degradation of tobacco.

Aerosol delivery devices or systems falling into the first sub-category of powered devices or systems may typically comprise a powered unit, comprising a heater element, which is arranged to heat a portion of a carrier that holds an aerosol precursor. The carrier comprises a substrate formed of a "wicking" material, which can absorb aerosol precursor liquid from a reservoir and hold the aerosol precursor liquid. Upon activation of the heater element, aerosol precursor liquid in the portion of the carrier in the vicinity of the heater element is vaporised and released from the carrier into an airstream flowing around the heater and carrier. Released aerosol precursor is entrained into the airstream to be borne by the airstream to an outlet of the device or system, from where it can be inhaled by a user.

The heater element is typically a resistive coil heater, which is wrapped around a portion of the carrier and is usually located in the liquid reservoir of the device or system. Consequently, the surface of the heater may always be in contact with the aerosol precursor liquid, and long-term exposure may result in the degradation of either or both of the liquid and heater. Furthermore, residues may build up upon the surface of the heater element, which may result in undesirable toxicants being inhaled by the user. Furthermore, as the level of liquid in the reservoir diminishes through use, regions of the heater element may become exposed and overheat.

The present invention has been devised in light of the above considerations.

BRIEF SUMMARY OF THE INVENTION

According to an aspect of the present invention, there is provided a fluid-transfer article comprising: a first region for holding an aerosol precursor and for transferring said aerosol precursor to an activation surface of a second region of said article, said activation surface being disposed at an end of said article configured for thermal interaction with a heater of an aerosol-generation apparatus; wherein at least said second region is formed from a polymeric wicking material.

Optionally, said first and second regions are both formed from said polymeric wicking material.

Conveniently, said polymeric wicking material comprises Polyetherimide (PEI).

Advantageously, said polymeric wicking material comprises Polyether ether ketone (PEEK).

Optionally, said polymeric wicking material comprises Polytetrafluoroethylene (PTFE).

Conveniently, said polymeric wicking material comprises Polyimide (PI).

Advantageously, said polymeric wicking material comprises Polyethersulphone (PES).

Optionally, said polymeric wicking material comprises Ultra-High Molecular Weight Polyethylene (UHMWPE).

Conveniently, said polymeric wicking material comprises Polypropylene (PP).

Advantageously, said polymeric wicking material comprises Polyethylene Terephthalate (PET).

Optionally, said polymeric wicking material is porous.

Conveniently, said material is configured such that pore diameter in said first region is greater than pore diameter in said second region.

Advantageously, said polymeric wicking material is heat resistant.

Optionally, said polymeric wicking material is a hydrophilic material that is configured to transfer fluid from said first region to said second region.

Conveniently, said polymeric wicking material is of greater hydrophilicity in said second region than said first region.

Advantageously, said polymeric wicking material is a sintered material.

Optionally, said polymeric wicking material comprises a graduated wicking action.

Conveniently, said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end.

Optionally, the fluid-transfer article is provided within a carrier for an aerosol precursor, the carrier comprising: a housing for engagement with an aerosol-generating apparatus, said housing being configured to provide a fluid pathway between a first end that is disposed in fluid engagement with an inlet of said aerosol-generating apparatus and a second end that is disposed in fluid engagement with an outlet of said aerosol-generating apparatus; the fluid-transfer article being provided within said housing.

Conveniently, the carrier is provided as part of an aerosol-delivery system, the system further comprising an aerosol-generation apparatus having a heater.

According to another aspect of the present invention, there is provided a fluid-transfer article comprising: a first region for holding an aerosol precursor and for transferring said aerosol precursor to an activation surface of a second region of said article, said activation surface being disposed at an end of said article configured for thermal interaction with a heater of an aerosol-generation apparatus; and a liquid-impermeable peripheral wall surrounding at least a portion of said first region; wherein said first region comprises a storage substrate in which said aerosol precursor is held; and wherein said peripheral wall and said storage substrate are formed integrally from the same material as a one-piece unit.

Optionally, said storage substrate is porous, and said peripheral wall is non-porous.

Conveniently, wherein said peripheral wall is defined by a skin formed from the material of said storage substrate.

Advantageously, said peripheral wall substantially completely circumscribes said storage substrate.

Optionally, at least said storage substrate is formed from porous material, an outermost surface of which has been treated to render it liquid impermeable and thereby define said peripheral wall.

Conveniently, said outermost surface is heat-treated.

Advantageously, said outermost surface is chemically treated.

Optionally, the article is provided in the form of a unitary monolithic element formed of said material, wherein said peripheral wall defines an outer surface of the fluid-transfer article across substantially the entire extent of said monolithic element, except said activation surface.

Conveniently, said material is a polymeric wicking material.

Advantageously, said first and second regions are both formed from said polymeric wicking material.

Optionally, said material comprises Polyetherimide (PEI).

Conveniently, said material comprises Polyether ether ketone (PEEK).

Optionally, said material comprises Polytetrafluoroethylene (PTFE).

Conveniently, said material comprises Polyimide (PI).

Advantageously, said material comprises Polyethersulphone (PES).

Optionally, said material comprises Ultra-High Molecular Weight Polyethylene (UHMWPE).

Conveniently, said material comprises Polypropylene (PP).

Advantageously, wherein said material comprises Polyethylene Terephthalate (PET).

Optionally, said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end.

Conveniently, the fluid-transfer article forms part of a carrier for an aerosol precursor.

Optionally, the carrier is provided in the form of a consumable for an aerosol-delivery system, wherein said storage substrate contains a liquid aerosol precursor.

Conveniently, the carrier is provided as part of an aerosol-delivery system, the system further comprising an aerosol-generation apparatus having a heater.

According to another aspect of the present invention, there is provided a fluid-transfer article comprising: a first region for holding an aerosol precursor and for transferring said aerosol precursor to an activation surface of a second region of said article, said activation surface being disposed at an end of said article configured for thermal interaction with a heating surface of an aerosol-generation apparatus; said activation surface including at least one angled surface portion and being configured such that, when the fluid-transfer article is arranged with respect to a said heating surface for thermal interaction therebetween, the or each said angled surface portion forms an acute intersection angle with said heating surface.

Optionally, said second region comprises at least one discontinuity in said activation surface to form a corresponding at least one channel between said activation surface and said heating surface, the or each said channel being configured for providing a fluid pathway across said activation surface, and being at least partly defined by a said angled surface portion in the form of a wall of the channel.

Conveniently, the or each said channel is at least partly defined by a pair of said angled surface portions, said pair of angled surface portions opposing one another across said channel to form opposite walls of the channel.

Advantageously, the or each said channel comprises a ceiling portion between said opposite walls of the channel.

Optionally, the ceiling portion of the or each said channel is substantially planar.

Conveniently, the ceiling portion of the or each said channel is substantially parallel to said heating surface.

Advantageously, said ceiling portion of the or each said channel is arcuate.

Optionally, the fluid-transfer article is provided in combination with a heater, wherein the heater comprises a substrate defining said heating surface, and at least one heating element formed on said heating surface.

Conveniently, the or each said heating element extends substantially adjacent a line at which a respective said angled surface portion intersects said heating surface.

Advantageously, the fluid-transfer article comprises a plurality of said angled surface portions, each said angled surface portion being configured to make a substantially equal intersection angle with said heating surface.

Optionally, the or each said intersection angle is greater than 10 degrees. Optionally, the or each said intersection angle is greater than 20 degrees. Optionally, the or each said intersection angle is greater than 30 degrees. Optionally, the or each said intersection angle is greater than 40 degrees. Optionally, the or each said intersection angle is greater than 50 degrees. Optionally, the or each said intersection angle is greater than 60 degrees. Optionally, the or each said intersection angle is greater than 70 degrees. Optionally, the or each said intersection angle is greater than 80 degrees. Optionally, the or each said intersection angle is less than 80 degrees. Optionally, the or each said intersection angle is less than 70 degrees. Optionally, the or each said intersection angle is less than 60 degrees. Optionally, the or each said intersection angle is less than 50 degrees. Optionally, the or each said intersection angle is less than 40 degrees. Optionally, the or each said intersection angle is less than 30 degrees. Optionally, the or each said intersection angle is less than 20 degrees. Optionally, the or each said intersection angle is less than 10 degrees.

Conveniently, at least said second region is formed from a polymeric wicking material.

Advantageously, said first and second regions are both formed from said polymeric wicking material.

Optionally, said polymeric wicking material is porous.

Conveniently, said polymeric wicking material is configured such that pore diameter in said first region is greater than pore diameter in said second region.

Advantageously, said polymeric wicking material is heat resistant.

Optionally, said polymeric wicking material is a hydrophilic material that is configured to transfer fluid from said first region to said second region.

Conveniently, said polymeric wicking material is of greater hydrophilicity in said second region than said first region.

Optionally, the fluid-transfer article forms part of a carrier for an aerosol precursor, the carrier comprising: a housing for engagement with an aerosol-generating apparatus, said housing being configured to provide a fluid pathway between a first end that is disposed in fluid engagement with an inlet of said aerosol-generating apparatus and a second end that is disposed in fluid engagement with an outlet of said aerosol-generating apparatus; wherein the fluid-transfer article is provided within said housing.

Conveniently, the carrier is provided as part of an aerosol-delivery system, the system further comprising an aerosol-generation apparatus having a heater defining a said heating surface.

According to another aspect of the present invention, there is provided a fluid-transfer article comprising: a first region for holding an aerosol precursor and for transferring said aerosol precursor to an activation surface of a second region of said article, said activation surface being disposed at an end of said article configured for thermal interaction with a heating surface of an aerosol-generation apparatus; said activation surface including at least one arcuate surface portion and being configured such that, when the fluid-transfer article is arranged with respect to a said heating surface for thermal interaction therebetween, the or each said arcuate surface portion opposes said heating surface and is concave towards said heating surface.

Optionally, said activation is configured such that, when the fluid-transfer article is arranged with respect to a said heating surface for thermal interaction therebetween, the or each said arcuate surface portion is spaced apart from said heating surface.

Conveniently, said second region comprises at least one discontinuity in said activation surface to form a corresponding at least one channel between said activation surface and said heating surface, the or each said channel being configured for providing a fluid pathway across said activation surface, and being at least partly defined by a respective said arcuate surface portion, said arcuate surface portion defining at least part of an internal surface of the channel.

Advantageously, the or each said channel is at least partly defined by a pair of spaced apart side walls, said arcuate surface portion extending between said wall portions to form a ceiling portion of said channel.

Optionally, said arcuate surface portion blends smoothly with each of said side walls, thereby eliminating a sharp corner therebetween.

Conveniently, said side walls are substantially planar.

Advantageously, the fluid-transfer article is provided in combination with a said heater, wherein the heater comprises a substrate defining said heating surface, and at least one heating element formed on said heating surface.

Optionally, the or each said heating element extends in substantial alignment with a respective said channel.

Conveniently, at least said second region is formed from a polymeric wicking material.

Advantageously, said first and second regions are both formed from said polymeric wicking material.

Optionally, said polymeric wicking material is porous.

Conveniently, said polymeric wicking material is configured such that pore diameter in said first region is greater than pore diameter in said second region.

Advantageously, said polymeric wicking material is heat resistant.

Optionally, said polymeric wicking material is a hydrophilic material that is configured to transfer fluid from said first region to said second region.

Conveniently, said polymeric wicking material is of greater hydrophilicity in said second region than said first region.

Optionally, the fluid-transfer article forms part of a carrier for an aerosol precursor, the carrier comprising: a housing for engagement with an aerosol-generating apparatus, said housing being configured to provide a fluid pathway between a first end that is disposed in fluid engagement with an inlet of said aerosol-generating apparatus and a second end that is disposed in fluid engagement with an outlet of said aerosol-generating apparatus; wherein the fluid-transfer article is provided within said housing.

Optionally, the carrier is provided as part of an aerosol-delivery system, the system further comprising an aerosol-generation apparatus having a said heater.

According to another aspect of the present invention, there is provided an aerosol-delivery system comprising: a heater having a heating surface; and a fluid-transfer article; said fluid-transfer article comprising a first region for holding an aerosol precursor and for transferring said aerosol precursor to an activation surface of a second region of said article; said activation surface being disposed for thermal interaction with said heating surface; said second region comprising a discontinuity in said activation surface to form a corresponding channel between said activation surface and said heating surface; said channel being configured to provide an airflow pathway across said activation surface; wherein said heater comprises a heating element located at said heating surface, said heating element being substantially aligned with said channel.

Optionally, said channel and said heating element are both elongate, said heating element being substantially parallel to a longitudinal axis of said channel.

Conveniently, said heating element is substantially aligned along a centreline of said channel.

Advantageously, said heating element is parallel to, but offset from, a centreline of said channel.

Optionally, said activation surface includes a plurality of said channels.

Conveniently, said heater comprises a plurality of said heating elements.

Advantageously, the or each said channel is aligned with at least one said heating element.

Optionally, the or each said channel is aligned with a plurality of said heating elements.

Conveniently, a pair of said heating elements are aligned with the or each said channel, each of said pair of heating elements being offset to opposite sides of the centreline of the channel.

Advantageously, said heating surface comprises at least one fluid transport region adjacent said heating element; the or each said fluid transport region being configured to move liquid across said heating surface towards the or each heating element.

Optionally, the or each said fluid transport region comprises hydrophobic material Conveniently, the or each said fluid transport region comprises a plurality of elongate regions of hydrophobic material.

Advantageously, said elongate regions of hydrophobic material are substantially parallel.

Optionally, the or each said heating element is substantially linear, and elongate regions of hydrophobic material are oriented substantially perpendicular to the or each said heating element.

Conveniently, the or each said fluid transport region comprises at least one capillary channel.

Advantageously, the or each said fluid transport region comprises a plurality of capillary channels.

Optionally, said capillary channels are substantially parallel.

Conveniently, the or each said capillary channel is formed in said heating surface as an open groove.

Optionally, the or each said heating element is substantially linear, and the or each said capillary channel is oriented substantially perpendicular to the or a said heating element.

Conveniently, the or each said heating element is a resistive heating filament.

According to another aspect of the present invention, there is provided an aerosol-generation apparatus, the apparatus comprising a heater having a planar heating surface, and being configured to receive an aerosol precursor carrier for thermal interaction with said heating surface; wherein said heater comprises a heating element at said heating surface, and said heating surface comprises a fluid transport region adjacent said heating element; said fluid transport region being configured to move liquid across said heating surface towards the heating element.

Optionally, said fluid transport region comprises hydrophobic material

Conveniently, said fluid transport region comprises a plurality of elongate regions of hydrophobic material.

Advantageously, said elongate regions of hydrophobic material are substantially parallel.

Optionally, said heating element is substantially linear, and said elongate regions of hydrophobic material are oriented substantially perpendicular to said heating element.

Conveniently, said fluid transport region comprises at least one capillary channel.

Advantageously, said fluid transport region comprises a plurality of capillary channels.

Optionally, said capillary channels are substantially parallel.

Conveniently, the or each said capillary channel is formed in said heating surface as an open groove.

Advantageously, said heating element is substantially linear, and the or each said capillary channel is oriented substantially perpendicular to said heating element.

Optionally, said heating element intersects the or each capillary channel.

Conveniently, said fluid transport region comprises porous material.

Optionally, said porous material is a porous ceramic.

Advantageously, said porous material is liquid-permeable.

Optionally, said porous material is provided in the form of a layer positioned on an underlying layer of liquid-impermeable material.

Conveniently, said layer of porous material extends beneath said heating element.

Advantageously, said heating element comprises a resistive heating filament.

Optionally, the aerosol-generation apparatus forms part of an aerosol-delivery system, the system further comprising a said carrier; the carrier comprising a fluid-transfer article; wherein said fluid-transfer article comprises a first region for holding an aerosol precursor and for transferring said aerosol precursor to an activation surface of a second region of said article, said activation surface being disposed at an end of said carrier configured for thermal interaction said heating surface; wherein said second region comprises at least one discontinuity in said activation surface to form a corresponding at least one air flow channel between said activation surface and said heating surface, said at least one air flow channel being configured to provide an airflow pathway across said activation surface.

Optionally, said heating element is substantially aligned with a said air flow channel formed by said discontinuity in said activation surface.

Conveniently, the or each said capillary channel extends at least from an edge of a said air flow channel to said heating element.

Advantageously, the or each said elongate region of hydrophobic material extends at least from an edge of a said air flow channel to said heating element.

According to another aspect of the present invention, there is provided an aerosol-generation apparatus, the apparatus comprising a heater having a heating surface, and being configured to receive an aerosol precursor carrier for thermal interaction with said heating surface; wherein said heater comprises a porous material defining at least a region said heating surface, and a heating element located upon said porous material at said heating surface.

Optionally, said porous material is a porous ceramic material.

Conveniently, said porous material defines substantially the entire extent of said heating surface.

Advantageously, said porous material is liquid-permeable.

Optionally, said heater comprises a supporting substrate on which said porous material is provided as a layer.

Conveniently, said supporting substrate is formed from substantially liquid-impermeable material.

Advantageously, said heater comprises a plurality of said heating elements upon said porous material.

Optionally, the or each said heating element comprises a resistive heating filament.

Conveniently, the aerosol-generation apparatus is provided as part of an aerosol-delivery system which further comprises a said carrier, the carrier comprising a fluid-transfer article; wherein said fluid-transfer article comprises a first region for holding an aerosol precursor and for transferring said aerosol precursor to an activation surface of a second region of said article, said activation surface being disposed at an end of said carrier configured for thermal interaction said heating surface; wherein the or each said heating element is located between said activation surface and said porous material defining the heating surface.

Optionally, at least a region of said activation surface contacts said porous material defining the heating surface.

Conveniently, said second region of said fluid-transfer article comprises at least one discontinuity in said activation surface to form a corresponding at least one air flow channel between said activation surface and said heating surface, said at least one air flow channel being configured to provide an airflow pathway across said activation surface.

Advantageously, the or each said heating element is aligned with a respective said air flow channel formed by said discontinuity in said activation surface.

According to another aspect of the present invention, there is provided an aerosol delivery system comprising: an aerosol-generation apparatus comprising: a receptacle for receiving a carrier; a heater; a carrier for an aerosol precursor comprising: a housing for location in said receptacle, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of said aerosol-generation apparatus; wherein said second region comprises at least one discontinuity in said activation surface to form a corresponding at least one channel between said activation surface and an opposing surface through which heat is conveyable to said activation surface from said heater, said at least one channel configured for providing a fluid pathway across said activation surface, said fluid pathway across said activation surface forming a portion of said fluid pathway between said first end and said second end.

Optionally, said article may comprise a tubular member. Further optionally, said article may comprise a bore extending therethrough, said first region extending axially along an external surface of said article and said second surface, located between said first region and said bore, extending axially along an internal surface of said article, said at least one discontinuity extending axially along said internal surface of said article formed by said bore. Yet further optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from said heater.

Optionally, said heater may comprise a planar heating surface.

Optionally, said heater may be a rod extending axially through said centre of said fluid-transfer article.

Optionally, said heater may comprise a collar arranged around said article.

Optionally, said collar may extend over a length of said article.

Optionally, said collar may extend over said second region of said article.

Optionally, said heater may comprise said opposing surface through which heat is conveyed to said activation surface, said heater in contact with said activation surface of said article.

Optionally, a thermally conductive barrier layer may be provided as said opposing surface through which heat is conveyable to said activation surface, said thermally conductive barrier layer in thermal contact with said heater and located between said heater and said activation surface of said article.

Optionally, said activation surface and said opposing surface through which heat is conveyable to said activation surface may be complementary. This may maintain a temperature gradient through the at least one channel for consistency of activation.

Optionally, said activation surface and said heater surface may be complementary.

Optionally, said article may be formed of a thermally conductive material.

Optionally, said article may be formed of a plastic material, such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures.

Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

Optionally, said heater may comprise a material of at least one of: a ceramic; and a metal. Optionally, a first end and a second end of said housing may be sealed with a removable end cap. The end caps are removable prior to the carrier being located in said apparatus.

Optionally, a first end and a second end of said housing may be sealed with a frangible barrier portion. The frangible barrier portion may be frangible so as to be penetrable for opening said carrier to atmosphere.

According to another aspect of the present invention, there is provided an aerosol-generation apparatus for use in the system as described above and hereinafter.

According to another aspect of the present invention, there is provided a carrier for an aerosol precursor comprising: a housing for location in a receptacle of an aerosol-generating apparatus, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of an aerosol-generation apparatus; wherein said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end.

Optionally, the article may comprise a tubular member.

Optionally, said article may comprise a bore extending therethrough, said first region extending axially along an external surface of said article and said second surface, located between said first region and said bore, extending axially along an internal surface of said article, said at least one discontinuity extending axially along said internal surface of said article formed by said bore.

Optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from a heater.

Optionally, a thermally conductive barrier layer may be provided as said opposing surface through which heat is conveyable to said activation surface, said thermally conductive barrier layer configured for thermal contact with a heater and locatable between a heater and said activation surface of said article.

Optionally, said activation surface and said opposing surface through which heat is conveyable to said activation surface may be complementary. This may maintain a temperature gradient through the at least one channel for consistency of activation.

Optionally, said article may be formed of a thermally conductive material.

Optionally, said article may be formed of a plastic material, such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures.

Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

Optionally, a first end and a second end of said housing may be sealed with a removable end cap. The end caps are removable prior to the carrier being located in said apparatus.

Optionally, a first end and a second end of said housing may be sealed with a frangible barrier portion. The frangible barrier portion may be frangible so as to be penetrable for opening said carrier to atmosphere.

According to another aspect of the present invention, there is provided a fluid-transfer article comprising: a first region for holding an aerosol precursor and for transferring said aerosol precursor to an activation surface of a second region of said article, said activation surface disposed at an end of said article configured for thermal interaction with a heater of an aerosol-generation apparatus; wherein said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end.

Optionally, the article may comprise a tubular member.

Optionally, the article may comprise a bore extending therethrough, said first region extending axially along an external surface of said article and said second surface, located between said first region and said bore, extending axially along an internal surface of said article, said at least one discontinuity extending axially along said internal surface of said article formed by said bore.

Optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from a heater.

Optionally, a thermally conductive barrier layer may be provided as said opposing surface through which heat is conveyable to said activation surface, said thermally conductive barrier layer configured for thermal contact with a heater and locatable between a heater and said activation surface of said article.

Optionally, said activation surface and said opposing surface through which heat is conveyable to said activation surface may be complementary. This may maintain a temperature gradient through the at least one channel for consistency of activation.

Optionally, said article may be formed of a thermally conductive material.

Optionally, said article may be formed of a plastic material, such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures.

Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

According to another aspect of the present invention, there is provided a kit-of-parts for assembling a system for aerosol delivery, comprising: an aerosol-generation apparatus comprising: a receptacle for receiving a carrier; a heater; a carrier for an aerosol precursor, said carrier locatable in said receptacle, and said carrier comprising: a housing for location in said receptacle, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of said aerosol-generation apparatus; wherein said second region comprises at least one discontinuity in said activation surface to form a corresponding at least one channel between said activation surface and an opposing surface through which heat is conveyable to said activation surface from said heater, said at least one channel configured for providing a fluid pathway across said activation surface, said fluid pathway across said activation surface forming a portion of said fluid pathway between said first end and said second end.

The invention includes the combination of the aspects and preferred features described except where such a combination is clearly impermissible or expressly avoided.

BRIEF DESCRIPTION OF THE SEVERAL VIEWS OF THE DRAWINGS

So that the invention may be more readily understood, and so that further features thereof may be appreciated, embodiments of the invention will now be described by way of example with reference to the accompanying drawings in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

In general outline, one or more embodiments in accordance with the present invention may provide a system for aerosol delivery in which an aerosol carrier may be inserted into a receptacle (e.g. a "heating chamber") of an apparatus for initiating and maintaining release of an aerosol from the aerosol carrier. Another end, or another end portion, of the aerosol carrier may protrude from the apparatus and can be inserted into the mouth of a user for the inhalation of aerosol released from the aerosol carrier cartridge during operation of the apparatus.

Hereinafter, and for convenience only, "system for aerosol delivery" shall be referred to as "aerosol delivery system".

Figure 1:
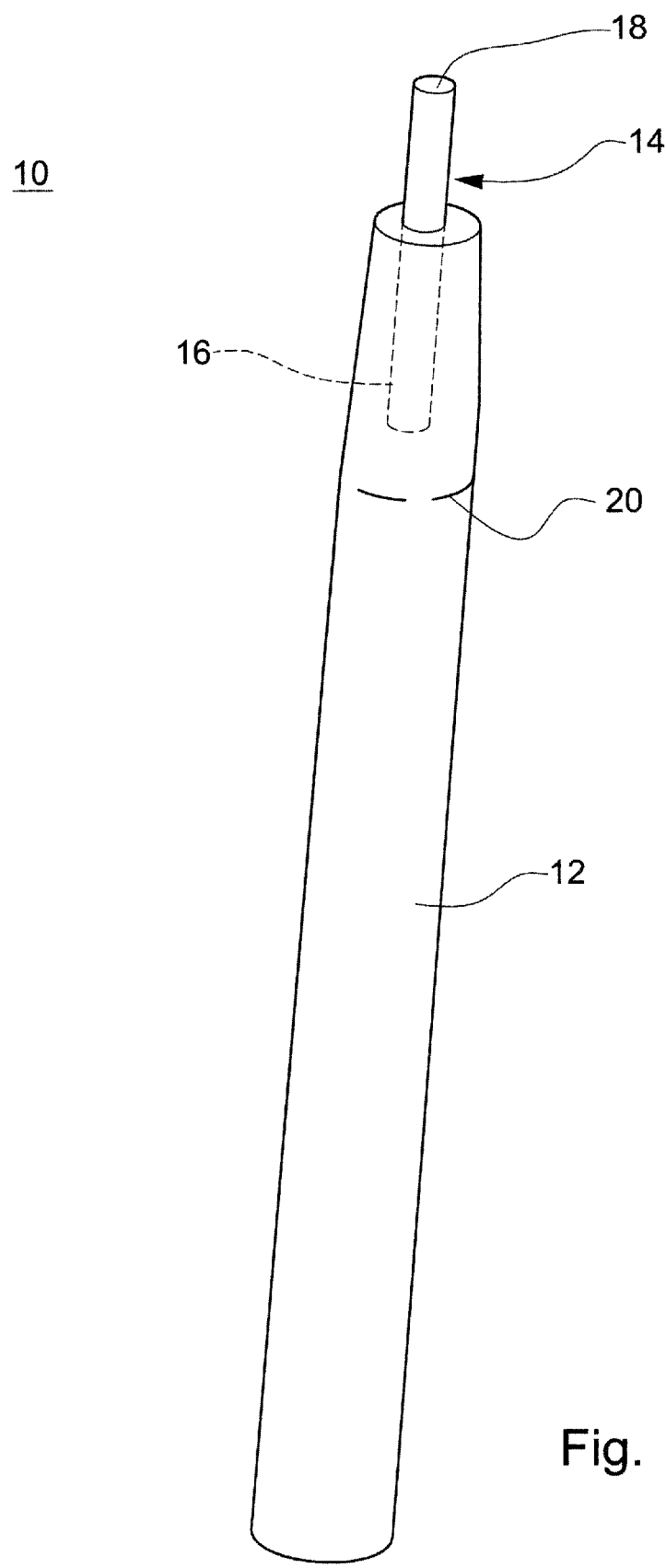
FIG. 1 is a perspective view illustration of a system for aerosol delivery according to one or more embodiments of the present invention.

Referring now to FIG. 1, there is illustrated a perspective view of an aerosol delivery system 10 comprising an aerosol generation apparatus 12 operative to initiate and maintain release of aerosol from a fluid-transfer article in an aerosol carrier 14. In the arrangement of FIG. 1, the aerosol carrier 14 is shown with a first end 16 thereof and a portion of the length of the aerosol carrier 14 located within a receptacle of the apparatus 12. A remaining portion of the aerosol carrier 14 extends out of the receptacle. This remaining portion of the aerosol carrier 14, terminating at a second end 18 of the aerosol carrier, is configured for insertion into a user's mouth. A vapour and/or aerosol is produced when a heater (not shown in FIG. 1) of the apparatus 12 heats a fluid-transfer article in the aerosol carrier 14 to release a vapour and/or an aerosol, and this can be delivered to the user, when the user sucks or inhales, via a fluid passage in communication with an outlet of the aerosol carrier 14 from the fluid-transfer article to the second end 18.

The apparatus 12 also comprises air-intake apertures 20 in the housing of the apparatus 12 to provide a passage for air to be drawn into the interior of the apparatus 12 (when the user sucks or inhales) for delivery to the first end 16 of the aerosol carrier 14, so that the air can be drawn across an activation surface of a fluid-transfer article located within a housing of the aerosol carrier 14 during use. Optionally, these apertures may be perforations in the housing of the apparatus 12.

A fluid-transfer article (not shown in FIG. 1, but described hereinafter with reference to FIGS. 5, 6, 7, 8, 9, 10, 11 and 12) is located within a housing of the aerosol carrier 14. The fluid-transfer article contains an aerosol precursor material, which may include at least one of: nicotine; a nicotine precursor material; a nicotine compound; and one or more flavourings. The fluid-transfer article is located within the housing of the aerosol carrier 14 to allow air drawn into the aerosol carrier 14 at, or proximal, the first end 16 to flow across an activation surface of the fluid-transfer article. As air passes across the activation surface of the fluid-transfer article, an aerosol may be entrained in the air stream from a substrate forming the fluid-transfer article, e.g. via diffusion from the substrate to the air stream and/or via vaporisation of the aerosol precursor material and release from the fluid-transfer article under heating.

The substrate forming the fluid-transfer article 34 comprises a porous material where pores of the porous material hold, contain, carry, or bear the aerosol precursor material. In particular, the porous material of the fluid-transfer article may be a polymeric wicking material such as, for example, a sintered material. Particular examples of material suitable for the fluid-transfer article include: Polyetherimide (PEI); Polytetrafluoroethylene (PTFE); Polyether ether ketone (PEEK); Polyimide (PI); Polyethersulphone (PES); and Ultra-High Molecular Weight Polyethylene. Other suitable materials may comprise, for example, BioVyon™ (by Porvair Filtration Group Ltd) and materials available from Porex®. Further optionally, a substrate forming the fluid-transfer article may comprise Polypropylene (PP) or Polyethylene Terephthalate (PET). All such materials may be described as heat resistant polymeric wicking material in the context of the present invention.

The aerosol carrier 14 is removable from the apparatus 12 so that it may be disposed of when expired. After removal of a used aerosol carrier 14, a replacement aerosol carrier 14 can be inserted into the apparatus 12 to replace the used aerosol carrier 14.

Figure 2:
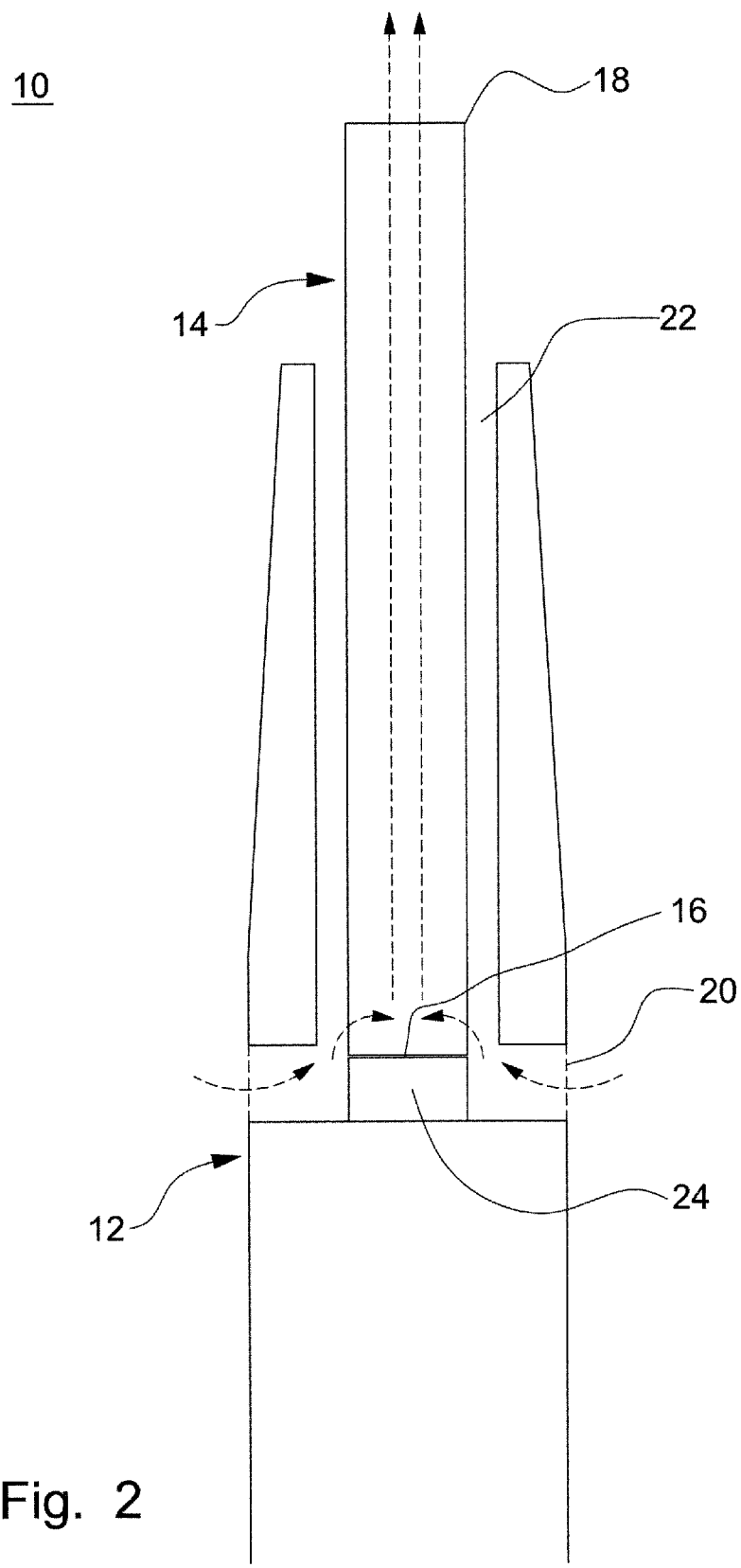
FIG. 2 is a cross-sectional side view illustration of part of an apparatus of the system for aerosol delivery of FIG. 1.

FIG. 2 is a cross-sectional side view illustration of a part of apparatus 12 of the aerosol delivery system 10. The apparatus 12 comprises a receptacle 22 in which is located a portion of the aerosol carrier 14. In one or more optional arrangements, the receptacle 22 may enclose the aerosol carrier 14. The apparatus 12 also comprise a heater 24, which opposes an activation surface of the fluid-transfer article (not shown in FIG. 2) of the aerosol carrier 14 when an aerosol carrier 14 is located within the receptacle 22.

Air flows into the apparatus 12 (in particular, into a closed end of the receptacle 22) via air-intake apertures 20. From the closed end of the receptacle 22, the air is drawn into the aerosol carrier 14 (under the action of the user inhaling or sucking on the second end 18) and expelled at the second end 18. As the air flows into the aerosol carrier 14, it passes across the activation surface of the fluid-transfer article. Heat from the heater 24, which opposes the activation surface of the fluid-transfer article, causes vaporisation of aerosol precursor material at the activation surface of the fluid-transfer article and an aerosol is created in the air flowing over the activation surface. Thus, through the application of heat in the region of the activation surface of the fluid-transfer article, an aerosol is released, or liberated, from the fluid-transfer article, and is drawn from the material of the aerosol carrier unit by the air flowing across the activation surface and is transported in the air flow to via outlet conduits (not shown in FIG. 2) in the housing of the aerosol carrier 14 to the second end 18. The direction of air flow is illustrated by arrows in FIG. 2.

To achieve release of the captive aerosol from the fluid-transfer article, the fluid-transfer article of the aerosol carrier 14 is heated by the heater 24. As a user sucks or inhales on second end 18 of the aerosol carrier 14, the aerosol released from the fluid-transfer article and entrained in the air flowing across the activation surface of the fluid-transfer article is drawn through the outlet conduits (not shown) in the housing of the aerosol carrier 14 towards the second end 18 and onwards into the user's mouth.

Figure 3:
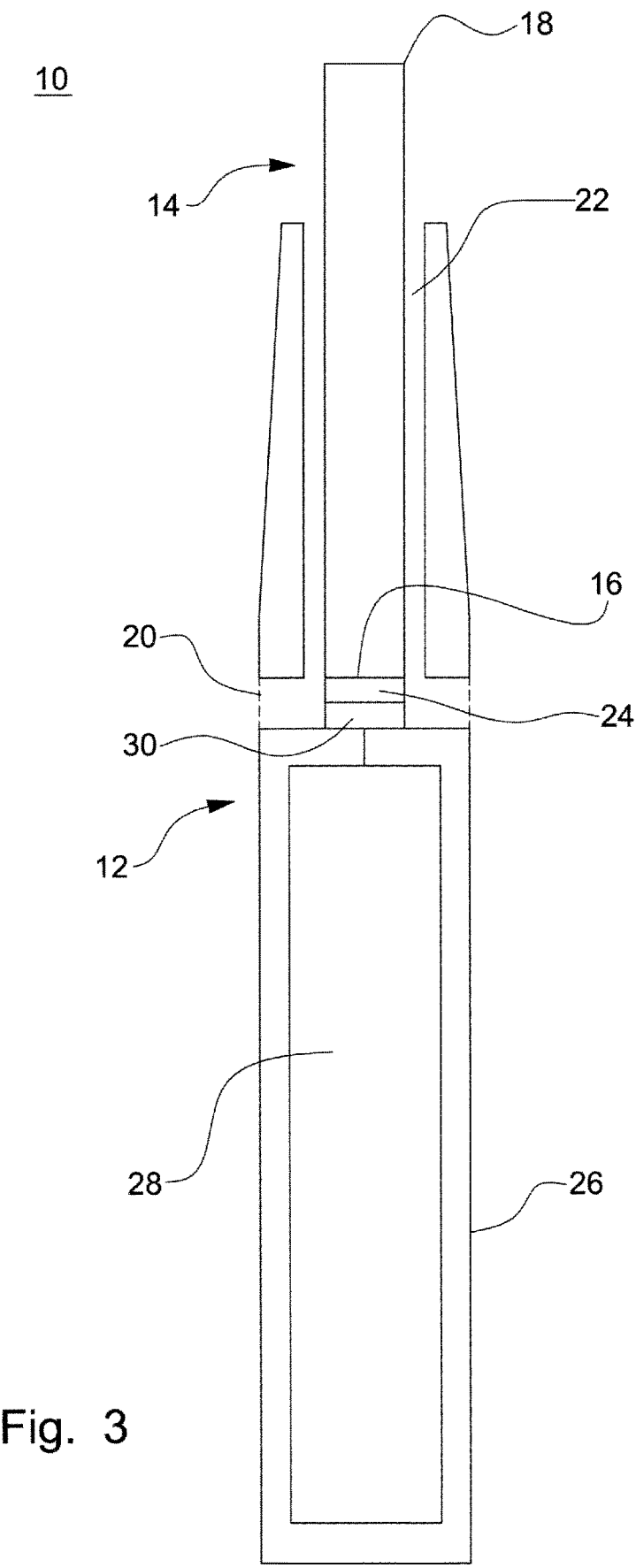
FIG. 3 is a cross-sectional side view illustration of the system and apparatus for aerosol delivery of FIG. 1.

Turning now to FIG. 3, a cross-sectional side view of the aerosol delivery system 10 is schematically illustrated showing the features described above in relation to FIGS. 1 and 2 in more detail.

As can be seen, apparatus 12 comprises a housing 26, in which are located the receptacle 22 and heater 24. The housing 26 also contains control circuitry (not shown) operative by a user, or upon detection of air and/or vapour being drawn into the apparatus 12 through air-intake apertures 20, i.e. when the user sucks or inhales. Additionally, the housing 26 comprises an electrical energy supply 28, for example a battery. Optionally, the battery comprises a rechargeable lithium ion battery. The housing 26 also comprises a coupling 30 for electrically (and optionally mechanically) coupling the electrical energy supply 28 to control circuitry (not shown) for powering and controlling operation of the heater 24.

Responsive to activation of the control circuitry of apparatus 12, the heater 24 heats the fluid-transfer article (not shown in FIG. 3) of aerosol carrier 14. This heating process initiates (and, through continued operation, maintains) release of vapour and/or an aerosol from the activation surface of the fluid-transfer article. The vapour and/or aerosol formed as a result of the heating process is entrained into a stream of air being drawn across the activation surface of the fluid-transfer article (as the user sucks or inhales). The stream of air with the entrained vapour and/or aerosol passes through the aerosol carrier 14 via outlet conduits (not shown) and exits the aerosol carrier 14 at second end 18 for delivery to the user.

This process is briefly described above in relation to FIG. 2, where arrows schematically denote the flow of the air stream into the apparatus 12 and through the aerosol carrier 14, and the flow of the air stream with the entrained vapour and/or aerosol through the aerosol carrier 14.

Figure 4:
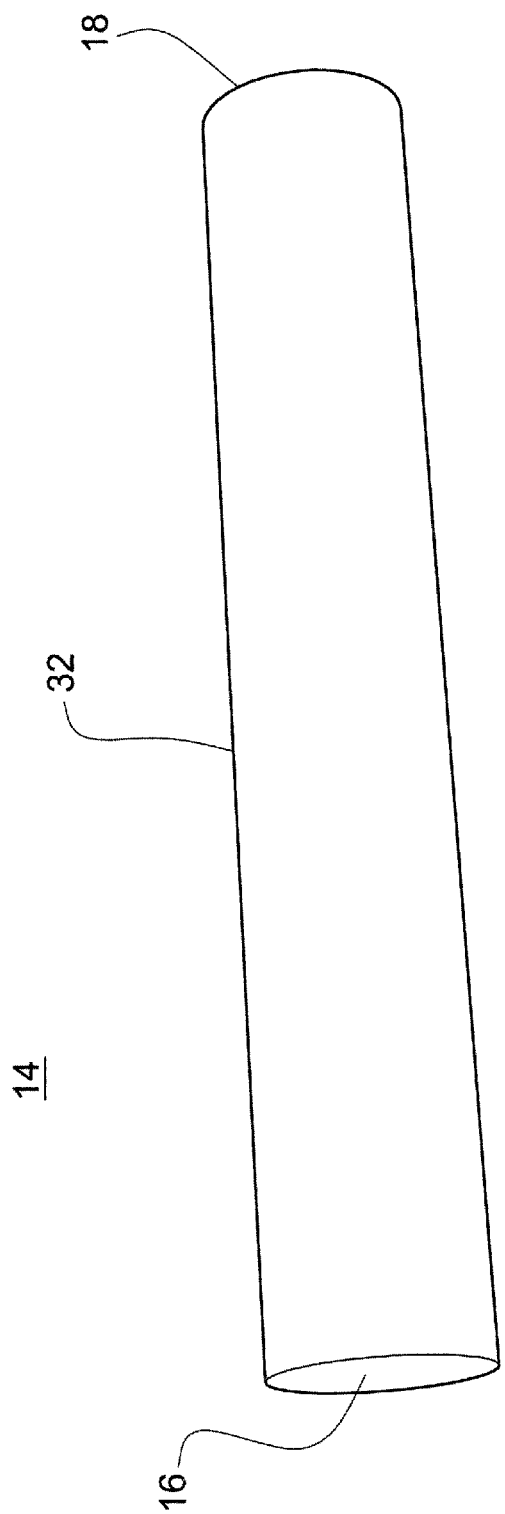
FIG. 4 is a perspective view illustration of an aerosol carrier for use in the system for aerosol delivery according to one or more embodiments of the present invention.
Figure 5:
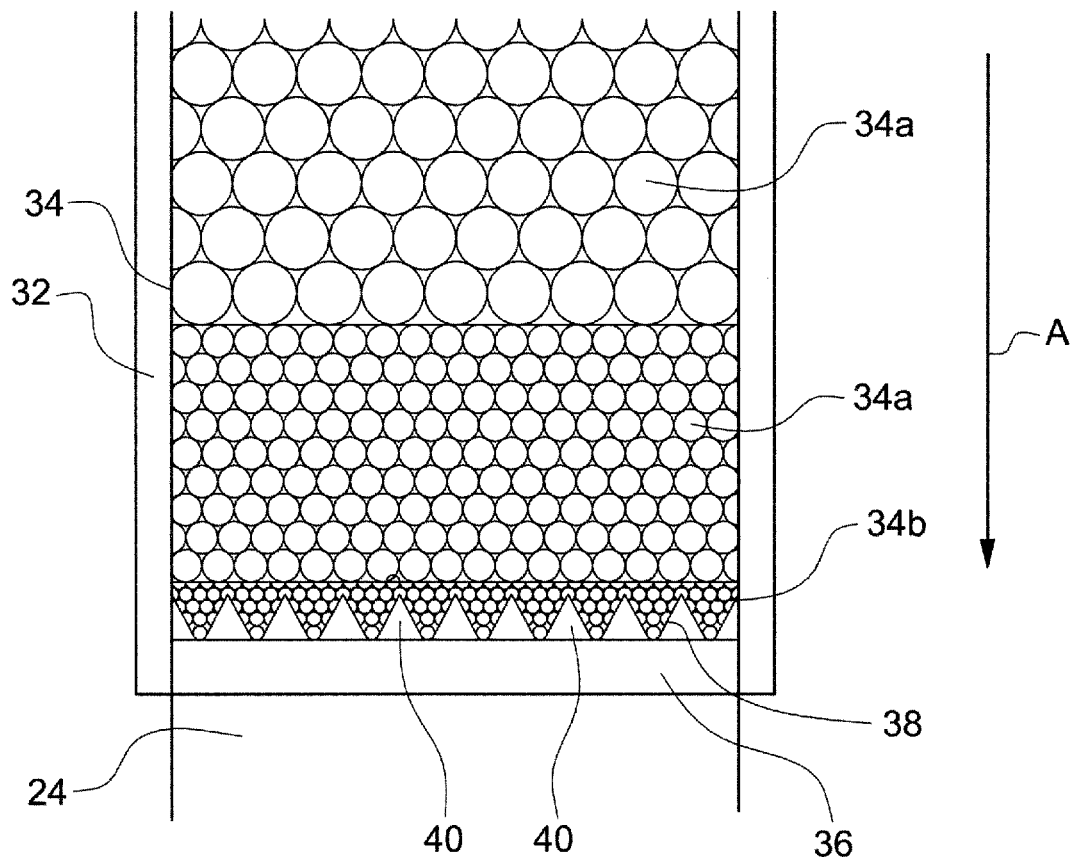
FIG. 5 is a cross-section side view of elements of an aerosol carrier and of part of an apparatus of the system for aerosol delivery according to one or more embodiments of the present invention.
Figure 6:
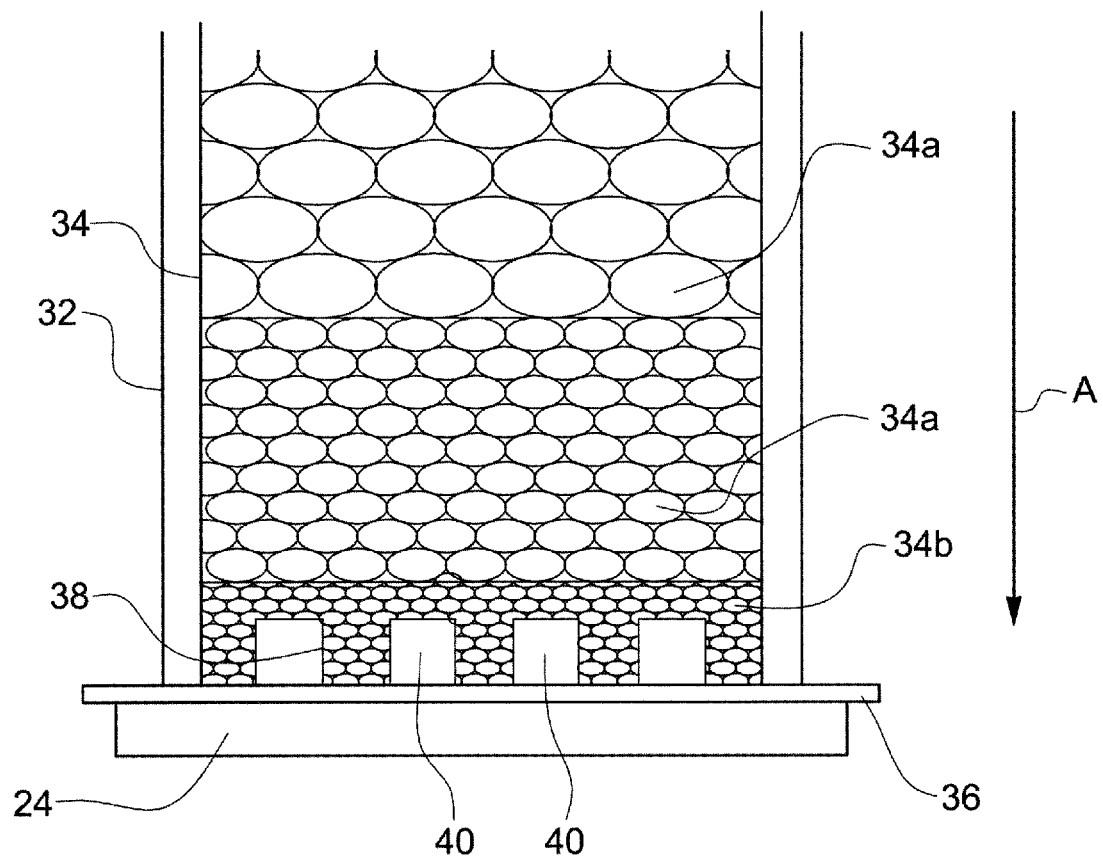
FIG. 6 is a cross-section side view of elements of an aerosol carrier and of part of an apparatus of the system for aerosol delivery according to one or more embodiments of the present invention.

FIGS. 4 to 6 schematically illustrate the aerosol carrier 14 in more detail (and, in FIGS. 5 and 6, features within the receptacle in more detail). FIG. 4 illustrates an exterior of the aerosol carrier 14, FIG. 5 illustrates internal components of the aerosol carrier 14 in an optional arrangement, and FIG. 6 illustrates internal components of the aerosol carrier 14 in another optional arrangement.

FIG. 4 illustrates the exterior of the aerosol carrier 14, which comprises a housing 32 for housing said fluid-transfer article (not shown) and at least one other internal component. The particular housing 32 illustrated in FIG. 4 comprises a tubular member, which may be generally cylindrical in form, and which is configured to be received within the receptacle of the apparatus. First end 16 of the aerosol carrier 14 is for location to oppose the heater of the apparatus, and second end 18 (and the region adjacent the second end 18) is configured for insertion into a user's mouth.

FIG. 5 illustrates some internal components of the aerosol carrier 14 and of the heater 24 of apparatus 12.

As described above, the aerosol carrier 14 comprises a fluid-transfer article 34. The aerosol carrier 14 optionally may comprise a conduction element 36 (as shown in FIG. 5). In one or more arrangements, the aerosol carrier 14 is located within the receptacle of the apparatus such that the activation surface of the fluid-transfer article opposes the heater of the apparatus and receives heat directly from the heater of the apparatus. In an optional arrangement, such as illustrated in FIG. 5 for example, the aerosol carrier 14 comprises a conduction element 36.

When aerosol carrier 14 is located within the receptacle of the apparatus such that the activation surface of the fluid-transfer article is located to oppose the heater of the apparatus, the conduction element is disposed between the heater 24 and the activation surface of the fluid-transfer article. Heat may be transferred to the activation surface via conduction through conduction element 36 (i.e. application of heat to the activation surface is indirect).

Further components not shown in FIGS. 5 and 6 (see FIGS. 11 and 12) comprise: an inlet conduit, via which air can be drawn into the aerosol carrier 14; an outlet conduit, via which an air stream entrained with aerosol can be drawn from the aerosol carrier 14; a filter element; and a reservoir for storing aerosol precursor material and for providing the aerosol precursor material to the fluid-transfer article 34.

In FIGS. 5 and 6, aerosol carrier is shown as comprising the fluid-transfer article 34 located within housing 32. The material forming the fluid-transfer article 34 comprises a porous structure, where pore diameter size varies between one end of the fluid-transfer article 34 and another end of the fluid-transfer article 34. In the illustrative examples of FIGS. 5 and 6, the pore diameter size gradually decreases from a first end remote from heater 24 (the upper end as shown in the figure) to a second end proximal heater 24 (the lower end as shown in the figure). Although the figure illustrates the pore diameter size changing in a step-wise manner from the first to the second end (i.e. a first region with pores having a diameter of a first size, a second region with pores having a diameter of a second, smaller size, and a third region with pores having a diameter of a third, yet smaller size), the change in pore size from the first end to the second end may be gradual rather than step-wise. This configuration of pores having a decreasing diameter size from the first end and second end can provide a wicking effect, which can serve to draw fluid from the first end to the second end of the fluid-transfer article 34.

The fluid-transfer article 34 comprises a first region 34a for holding an aerosol precursor. In one or more arrangements, the first region 34a of the fluid-transfer article 34 comprises a reservoir for holding the aerosol precursor. The first region 34a can be the sole reservoir of the aerosol carrier 14, or it can be arranged in fluid communication with a separate reservoir, where aerosol precursor is stored for supply to the first region 34a.

The fluid-transfer article 34 also comprises a second region 34b. Aerosol precursor is drawn from the first region 34a to the second region 34b by the wicking effect of the substrate material forming the fluid-transfer article. Thus, the first region 34a is configured to transfer the aerosol precursor to the second region 34b of the article 34.

At the second end of fluid-transfer article 34, the surface of the second region 34b defines an activation surface 38, which is disposed opposite a surface for conveying heat to the activation surface 38. In the illustrative examples of FIGS. 5 and 6, the opposing surface for conveying heat to the activation surface 38 comprises a conduction element 36. The conduction element 36 is located for thermal interaction with heater 24 and is arranged to transfer heat from heater 24 to the activation surface 38. As noted above, however, the conduction element 36 may be absent in some arrangements, in which case the activation surface 38 is disposed to receive heat directly from heater 24.

The conduction element 36, if present, may comprise a thin film of thermally conductive material, such as, for example, a metal foil (for example, aluminium, brass, copper, gold, steel, silver, or an alloy comprising anyone of the foregoing together with thermally conductive plastics and/or ceramics).

The activation surface 38 is discontinuous such that at least one channel 40 is formed between the activation surface 38 and the conduction element 36 (or the heater 24 in the case of arrangements in which the conduction element 36 is absent). In some arrangements, the discontinuities may be such that the activation surface 38 is undulating.

In the illustrative examples of FIGS. 5 and 6, the activation surface 38 comprises a plurality of grooves or valleys therein to form an undulating surface, the grooves or valleys being disposed in a parallel arrangement across the activation surface 38. Thus, there are a plurality of channels 40 between the activation surface 38 and the conduction element 36.

In the illustrative example of FIG. 5, the grooves or valleys in the activation surface 38 provide alternating peaks and troughs that give rise to a "saw-tooth" type profile. In one or more optional arrangements, the activation surface may comprise a "castellated" type profile (i.e. a "square wave" type profile), for example, such as illustrated in the example of FIG. 6. In one or more optional arrangements, the activation surface may comprise a "sinusoidal" type profile. The profile may comprise a mixture of two or more of the above profiles given as illustrative examples.

In the illustrative examples of FIGS. 5 and 6, the first region 34a of the fluid-transfer article 34 is located at an "upstream" end of the fluid-transfer article 34 and the second region 34b is located at a downstream" end of the fluid-transfer article 34. That is, aerosol precursor is wicked, or is drawn, from the "upstream" end of the fluid-transfer article 34 to the "downstream" end of the fluid-transfer article 34 (as denoted by arrow A in FIG. 5).

The aerosol precursor is configured to release an aerosol and/or vapour upon heating. Thus, when the activation surface 38 receives heat conveyed from heater 24, the aerosol precursor held at the activation surface 38 is heated. The aerosol precursor, which is captively held in material of the fluid-transfer article at the activation surface 38 is released into an air stream flowing through the channels 40 between the conduction element 36 and activation surface 38 (or between the heater 24 and the activation surface 38) as an aerosol and/or vapour.

The shape and/or configuration of the activation surface 38 and the associated shape(s) and/or configuration(s) of the one or more channels 40 formed between the activation surface 38 and conduction element 36 (or between the activation surface 38 and heater 24) permit air to flow across the activation surface 38 (through the one or more channels 40) and also increase the surface area of the activation surface 38 of the fluid-transfer article 34 that is available for contact with a flow of air across the activation surface 38.

Figure 7:
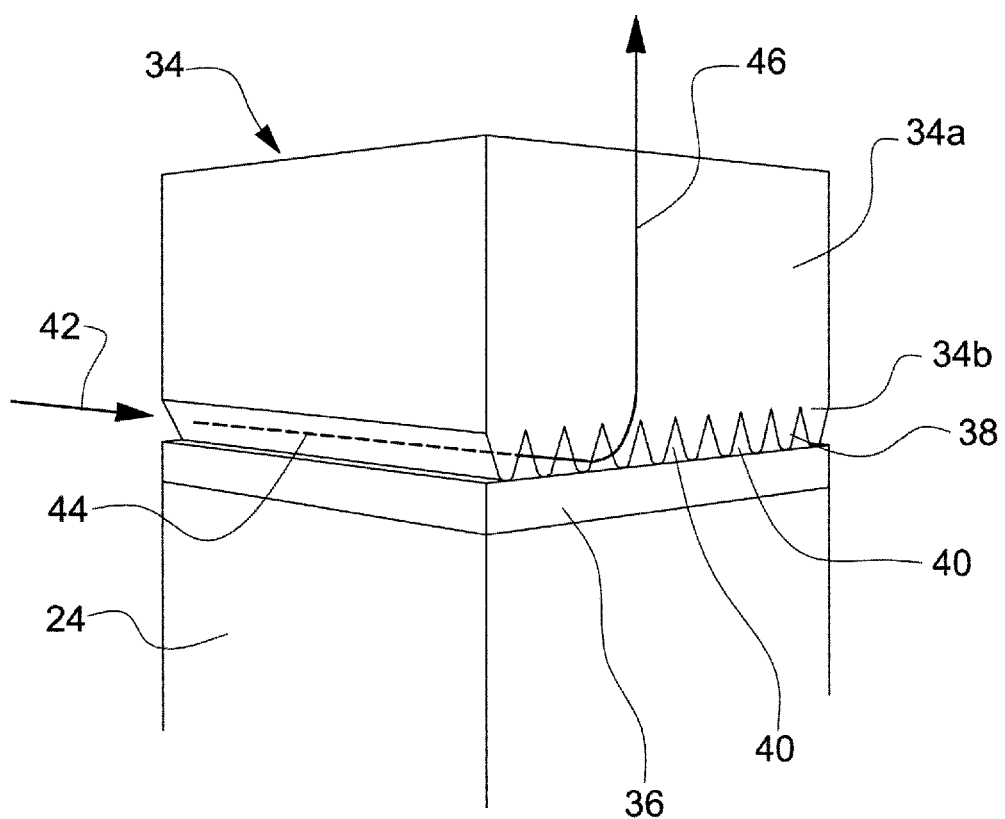
FIG. 7 is a perspective view illustration of the aerosol carrier and of part of an apparatus of the system for aerosol delivery according to one or more embodiments of the present invention.
Figure 8:
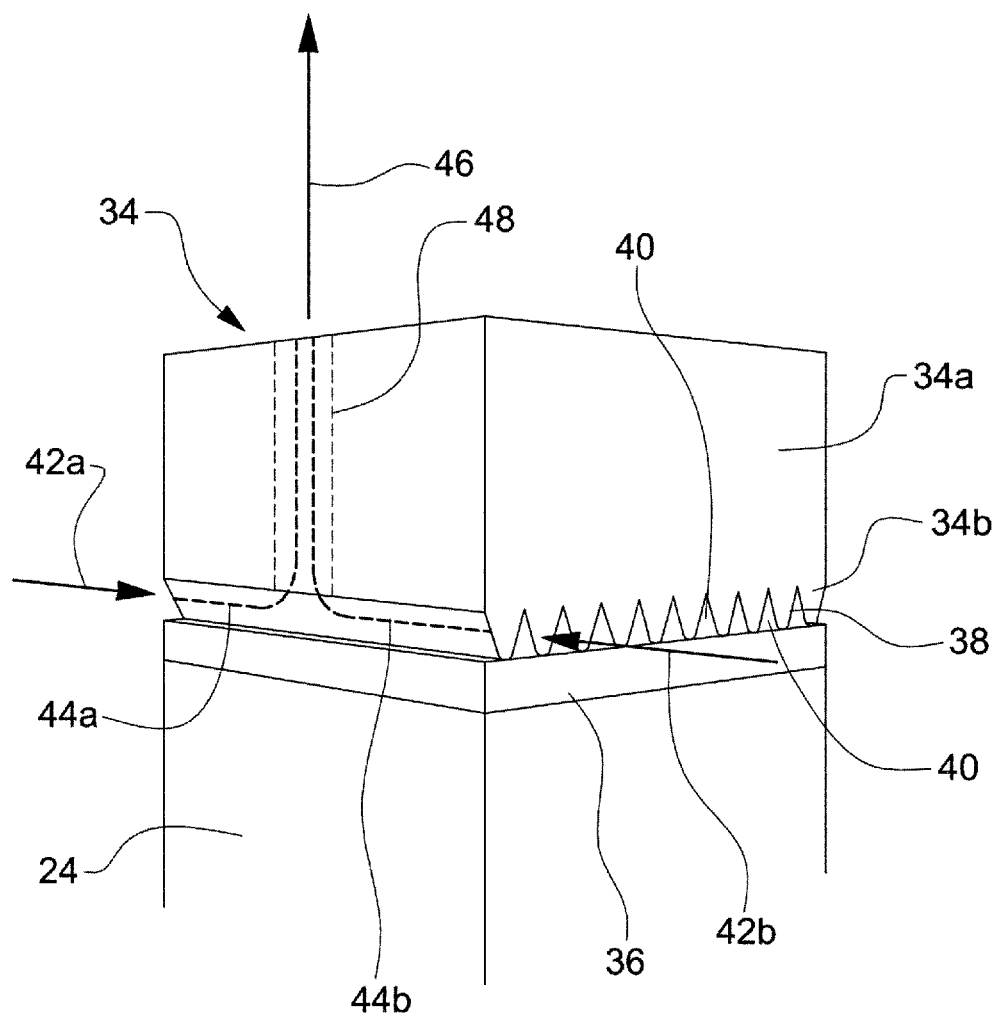
FIG. 8 is a perspective view illustration of the aerosol carrier and of part of an apparatus of the system for aerosol delivery according to one or more embodiments of the present invention.

FIGS. 7 and 8 show perspective view illustrations of the fluid-transfer article 34 of aerosol carrier and a heater 24 of the apparatus of the system for aerosol delivery. In particular, these figures illustrate air flows across the activation surface 38 when the apparatus is in use in a first arrangement of the fluid-transfer article 34 (see FIG. 7), and in a second arrangement of the fluid-transfer article 34 (see FIG. 8).

In the illustrated example of use of the apparatus schematically illustrated in FIG. 7, when a user sucks on a mouthpiece of the apparatus, air is drawn into the carrier through inlet apertures (not shown) provided in a housing of the carrier. An incoming air stream 42 is directed to the activation surface 38 of the fluid-transfer article 34 (e.g. via a fluid communication pathway within the housing of the carrier). When the incoming air stream 42 reaches a first side of the activation surface 38, the incoming air stream 42 flows across the activation surface 38 via the one or more channels 40 formed between the activation surface 38 and the conduction element 36 (or between the activation surface 38 and heater 24). The air stream 44 flowing through the one or more channels 40 is denoted by a dashed line in FIG. 7. As the air stream 44 flows through the one or more channels 40, aerosol precursor at activation surface 38, across which the air stream 44 flows, is released from the activation surface 38 by heat conveyed to the activation surface from the heater 24. Aerosol precursor released from the activation surface 38 in this manner is then entrained in the air stream 44 flowing through the one or more channels 40. In use, the heater 24 of the apparatus 12 conveys heat to the fluid-transfer article 34 to raise the temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article. As the air stream 44 continues its passage in the one or more channels 40, more released aerosol precursor is entrained within the air stream 44. When the air stream 44 entrained with aerosol precursor exits the one or more channels 40 at a second side of the activation surface 38, it is directed to an outlet, from where it can be inhaled by the user via a mouthpiece. An outgoing air stream 46 entrained with aerosol precursor is directed to the outlet (e.g. via a fluid communication pathway within the housing of the carrier).

Therefore, operation of the apparatus will cause heat from the heater 24 to be conveyed to the activation surface 38 of the fluid-transfer article. At a sufficiently high temperature, captive substances held at the activation surface 38 of the fluid-transfer article 34 are released, or liberated, to form a vapour and/or aerosol. Thus, when a user draws on a mouthpiece of the apparatus, the released substances from the fluid-transfer article are drawn away from the activation surface 38 (entrained in a stream of air) and condense to form an aerosol that is drawn through the a gas communication pathway for delivery to an outlet, which is in fluid communication with the mouthpiece.

As the aerosol precursor is released from the activation surface 38, a wicking effect of the fluid-transfer article 34 causes aerosol precursor within the body of the fluid-transfer article to migrate to the activation surface 38 to replace the aerosol precursor released from the activation surface 38 into air stream 44.

Operation of the heater 24 is controlled by control circuitry (not shown), which is operable to actuate the heater 24 responsive to an actuation signal from a switch operable by a user or configured to detect when the user draws air through a mouthpiece of the apparatus by sucking or inhaling. In an optional arrangement, the control circuitry operates to actuate the heater 24 with as little delay as possible from receipt of the actuation signal from the switch, or detection of the user drawing air through the mouthpiece. This may effect near instantaneous heating of the activation surface 38 of the fluid-transfer article 34.

In the illustrated example of use of the apparatus schematically illustrated in FIG. 8, rather than the case of FIG. 7, where air is drawn toward the activation surface 38 from one side only (and exits from the one or more channels 40 at an opposite side), a gas communication pathway for an incoming air stream is configured to deliver the incoming air stream to the activation surface 38 from both sides of the fluid-transfer article, and thus from both ends of the channels 40 formed therein. In such an arrangement, a gas communication pathway for an outlet airstream may be provided through the body of the fluid-transfer article 34. An outlet fluid communication pathway for an outlet airstream in the illustrative example of FIG. 8 is denoted by reference number 48.

Thus, in the illustrative example of FIG. 8, when a user draws on a mouthpiece of the apparatus, air is drawn into the aerosol carrier 14 through inlet apertures (not shown) provided in a housing of the carrier. An incoming air stream 42a from a first side is directed to a first side of the activation surface 38 of the fluid-transfer article 34 (e.g. via a gas communication pathway within the housing of the aerosol carrier 14). An incoming air stream 42b from a second side is directed to a second side of the activation surface 38 of the fluid-transfer article 34 (e.g. via a gas communication pathway within the housing of the aerosol carrier 14). When the incoming air stream 42a from the first side reaches the first side of the activation surface 38, the incoming air stream **42*a* flows across the activation surface 38 via the one or more channels 40 formed between the activation surface 38 and the conduction element 36 (or between the activation surface 38 and heater 24). Likewise, when the incoming air stream 42*b* from the second side reaches the second side of the activation surface 38, the incoming air stream 42*b* flows across the activation surface 38 via the one or more channels 40 formed between the activation surface 38 and the conduction element 36 (or between the activation surface 38 and heater 24). The air streams 44*a* and 44*b* from each side flowing through the one or more channels 40 are denoted by dashed lines in FIG. 8. As air streams 44*a* and 44*b* flow through the one or more channels 40, aerosol precursor in the activation surface 38, across which the air streams 44*a* and 44*b* flow, is released from the activation surface 38** by heat conveyed to the activation surface from the heater 24. Aerosol precursor released from the activation surface 38 is entrained in air streams 44a and 44b flowing through the one or more channels 40. In use, the heater 24 of the apparatus 12 conveys heat to the fluid-transfer article 34 to raise a temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article. As the air streams 44a and 44b continue their passages in the one or more channels 40, more released aerosol precursor is entrained within the air streams 44a and 44b. When the air streams 44a and 44b entrained with aerosol precursor meet at a mouth of the outlet fluid communication pathway 48, they enter the outlet fluid communication pathway 48 and continue until they exit outlet fluid communication pathway 48, either as a single outgoing air stream 46 (as shown), or as separate outgoing air streams. The outgoing air stream 46 is directed to an outlet, from where it can be inhaled by the user via a mouthpiece. The outgoing air stream 46 entrained with aerosol precursor is directed to the outlet (e.g. via a gas communication pathway within the housing of the aerosol carrier 14).

Figure 9:
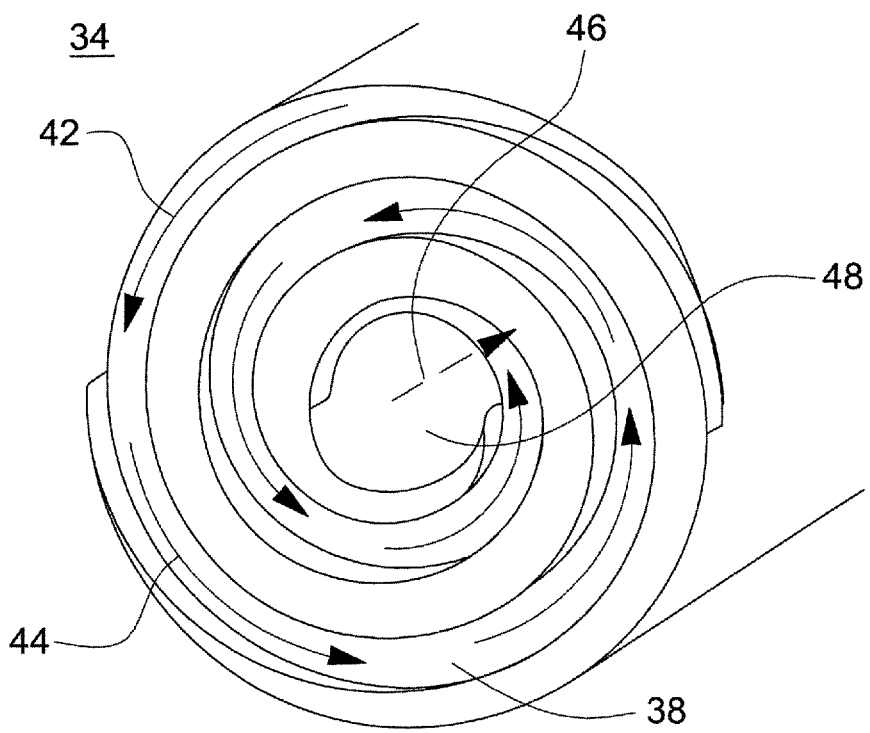
FIG. 9 is a perspective end view illustration of a fluid-transfer article of the aerosol carrier according to one or more embodiments of the present invention.
Figure 10:
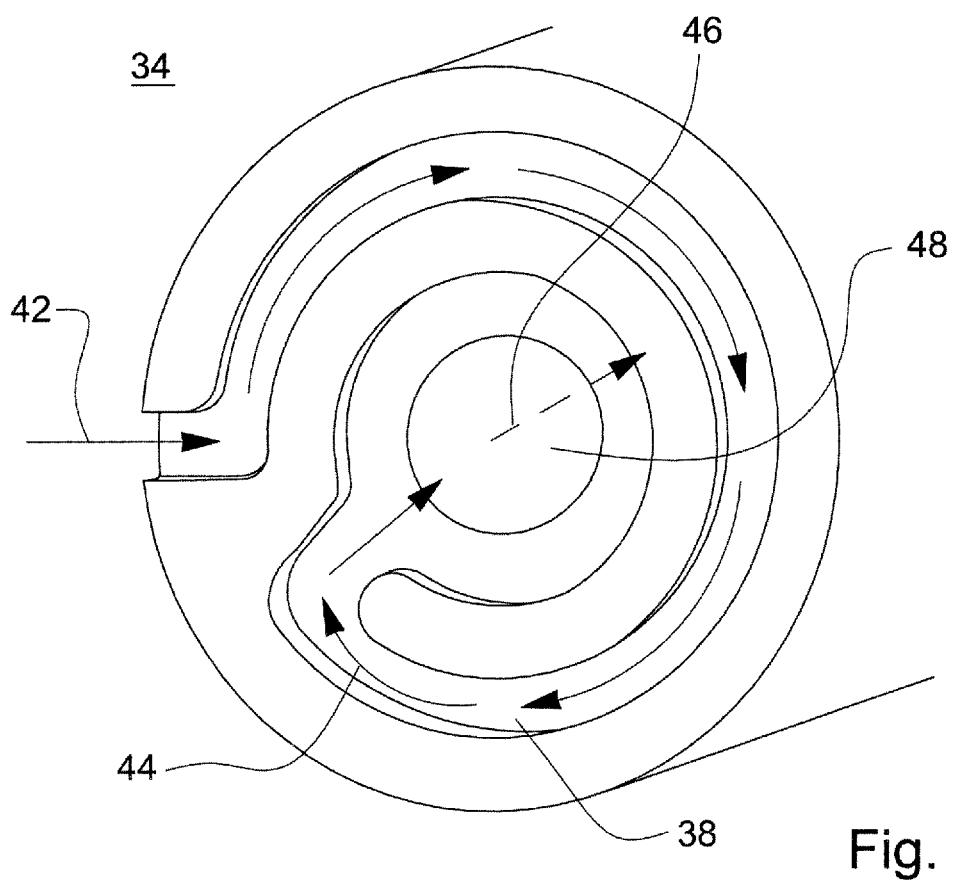
FIG. 10 is a perspective end view illustration of a fluid-transfer article of the aerosol carried according to one or more embodiments of the present invention.

FIGS. 9 and 10 are perspective end view illustrations of a fluid-transfer article 34 of the aerosol carrier according to one or more arrangements. These figures show different types of channel configurations as illustrative examples. In both illustrative examples of a channel configuration, as shown in FIGS. 9 and 10, the fluid-transfer article 34 comprises a cylindrical member, which comprises a central bore extending therethrough for fluid communication between the activation surface 38 and an outlet, from where an outgoing air stream can be delivered for inhalation. The central bore serves as an outlet fluid communication pathway 48 (e.g. as described above in relation to FIG. 9).

In both illustrative examples of FIGS. 9 and 10, an incoming air stream 42 is directed to a mouth of a channel 40 formed between the activation surface 38 of the fluid-transfer article 34 and conduction element (not shown), or between the activation surface 38 and a heater (not shown). In both illustrative examples of FIGS. 9 and 10, the mouth of the channel 40 is located at an outer edge of the fluid-transfer article 34 and an exit from the channel 40 (in fluid communication with the outlet fluid communication pathway 48) is located toward a centre of the fluid-transfer article. Therefore, the incoming air stream 42 enters the channel 40 via channel mouth at the outer edge of the fluid-transfer article 34 and moves toward the centre of the fluid-transfer article 34 as directed by the channel 40. As described above, as the air stream passes across activation surface 38 through channel 40, aerosol precursor is released from the activation surface 38 and is entrained in air stream 44. Air stream 44 continues to flow through the channel 40 until it reaches an exit thereof, from where it enters the outlet fluid communication pathway 48 and proceeds as an outgoing air stream 46 entrained with aerosol precursor toward the outlet.

In both illustrative examples of FIGS. 9 and 10, the valleys or grooves of the activation surface 38 that form part of the channel 40 are arranged to define a circuitous route 20 across the activation surface. In the illustrative examples, the route is a spiral path, but in optional arrangements, may be meandering or circuitous in some other manner. In optional arrangements, the activation surface may be located to face outwardly from the cylinder, such that the groove(s) or valley(s) may be in the outer surface of the cylinder forming the fluid-transfer article. These grooves or valleys may be arranged in parallel in a direction along the length of the cylinder. The groove(s) or valley(s) may be arranged in a spiral manner around the outside of the cylinder. In optional arrangements, the activation surface 38 may be located to face inwardly from the cylinder (i.e. surrounding the central bore), such that the groove(s) or valley(s) may be in the inner surface of the cylinder forming the fluid-transfer article 34. These grooves or valleys may be arranged in parallel in a direction along the length of the cylinder. The groove(s) or valley(s) may be arranged in a spiral manner around the inside of the cylinder.

Figure 11:
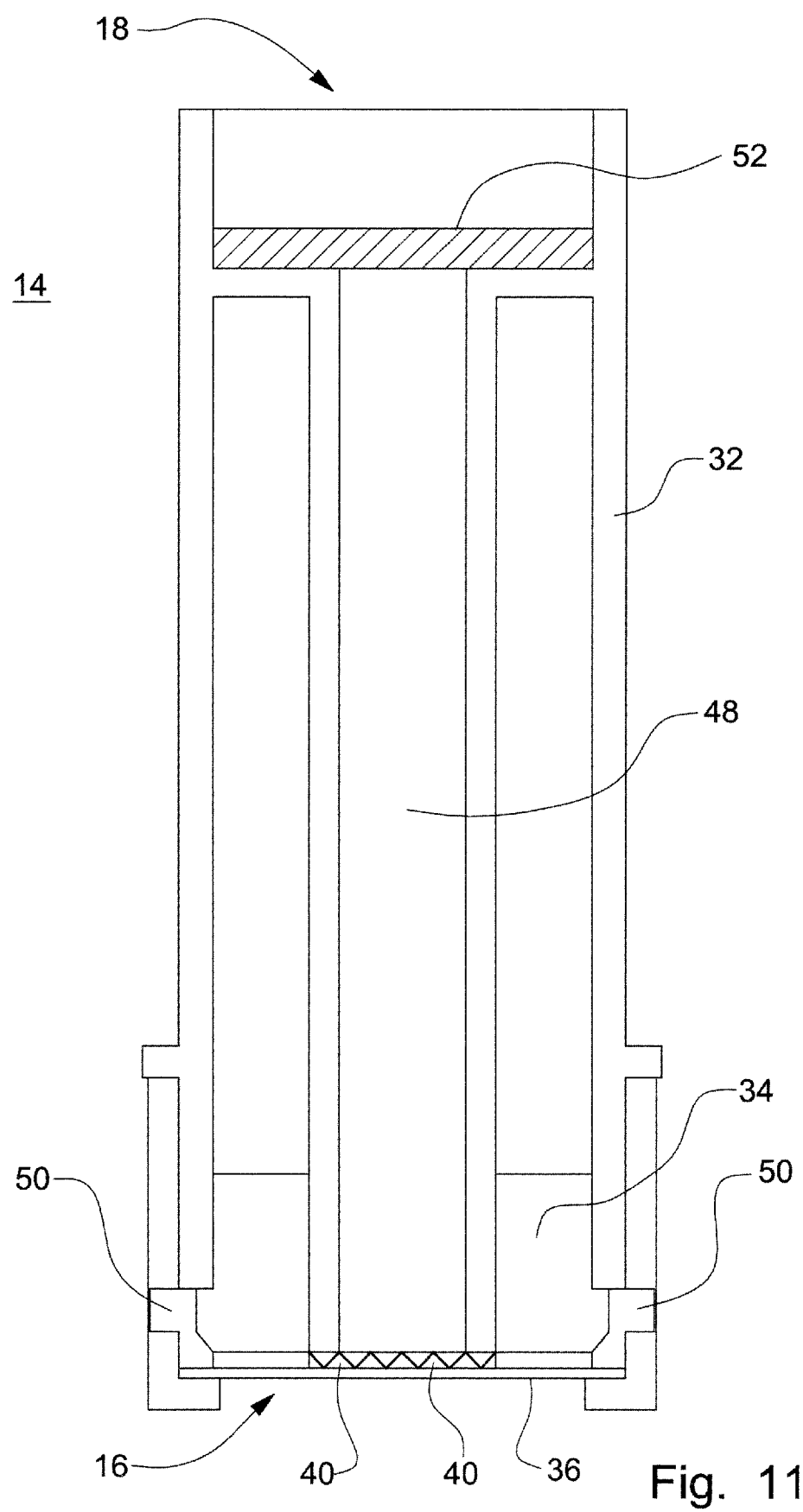
FIG. 11 is a cross-section side view of an aerosol carrier according to one or more embodiments of the present invention.
Figure 12:
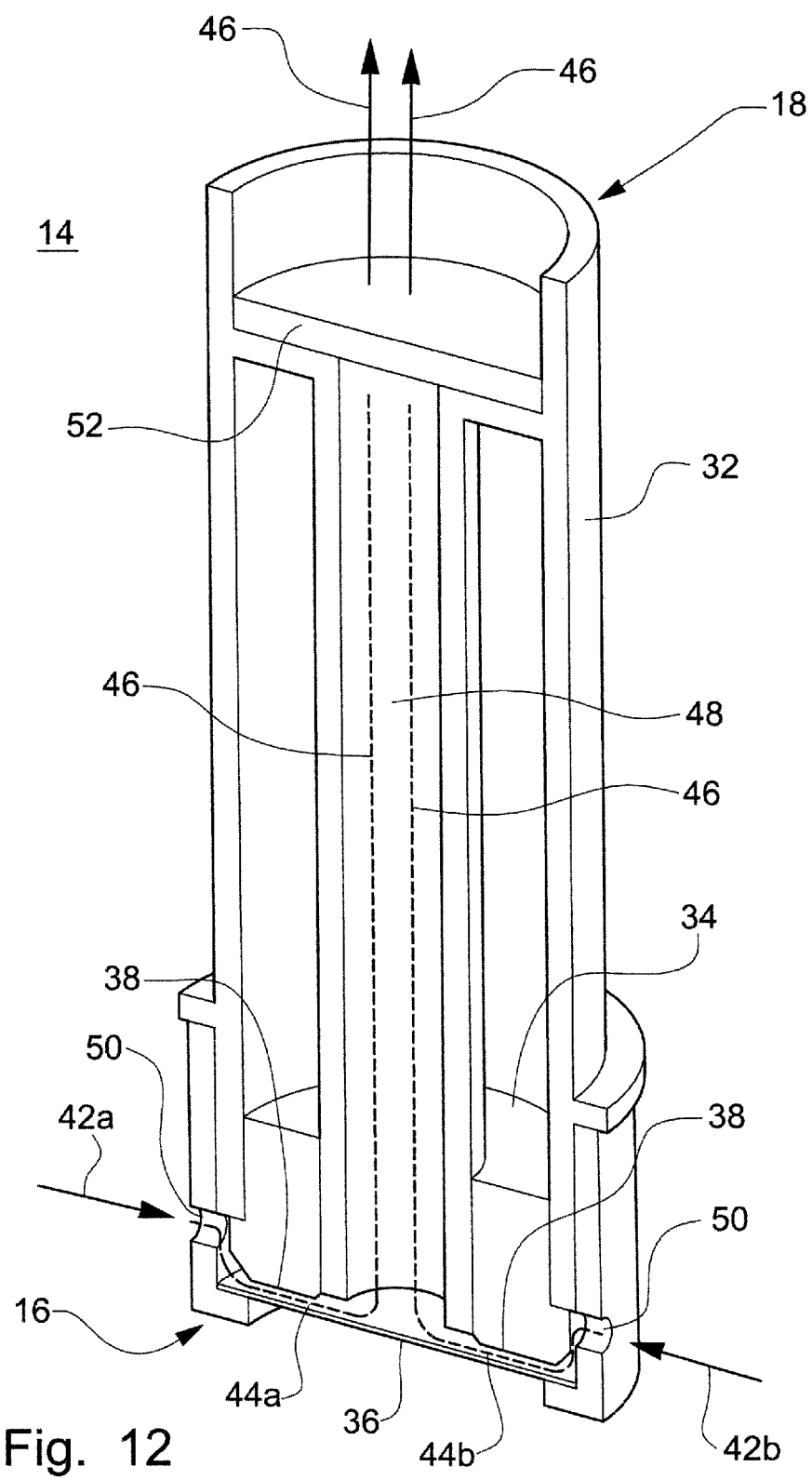
FIG. 12 is a perspective cross-section side view of the aerosol carrier of FIG. 11.

FIGS. 11 and 12 illustrate an aerosol carrier 14 according to one or more possible arrangements in more detail. FIG. 11 is a cross-section side view illustration of the aerosol carrier 14 and FIG. 12 is a perspective cross-section side view illustration of the aerosol carrier 14 of FIG. 11.

As can be seen from FIGS. 11 and 12, the aerosol carrier 14 is generally tubular in form. The aerosol carrier 14 comprises housing 32, which defines the external walls of the aerosol carrier 14 and which defines therein a chamber in which are disposed the fluid-transfer article 34 (adjacent the first end 16 of the aerosol carrier 14) and internal walls defining the outlet fluid communication pathway 48. Outlet fluid communication pathway 48 defines a fluid pathway for an outgoing air stream from the channels 40 to the second end 18 of the aerosol carrier 14. In the examples illustrated in FIGS. 11 and 12, the fluid-transfer article 34 is an annular shaped element located around the outlet fluid communication pathway 48.

In walls of the housing 32, there are provided inlet apertures 50 to provide a fluid communication pathway for an incoming air stream to reach the fluid-transfer article 34, and particularly the one or more channels 40 defined between the activation surface of the fluid-transfer article 34 and the conduction element 36 (or between the activation surface and the 15 heater).

In the illustrated example of FIGS. 11 and 12, the aerosol carrier 14 further comprises a filter element 52. The filter element 52 is located across the outlet fluid communication pathway 48 such that an outgoing air stream passing through the outlet fluid communication pathway 48 passes through the filter element 52.

With reference to FIG. 12, when a user sucks on a mouthpiece of the apparatus (or on the second end 18 of the aerosol carrier 14, if configured as a mouthpiece), air is drawn into the carrier through inlet apertures 50 extending through walls in the housing 32 of the aerosol carrier 14. An incoming air stream 42a from a first side of the aerosol carrier 14 is directed to a first side of the activation surface 38 of the fluid-transfer article 34 (e.g. via a gas communication pathway within the housing of the carrier). An incoming air stream 42b from a second side of the aerosol carrier 14 is directed to a second side of the activation surface 38 of the fluid-transfer article 34 (e.g. via a gas communication pathway within the housing of the carrier). When the incoming air stream 42a from the first side of the aerosol carrier 14 reaches the first side of the activation surface 38, the incoming air stream 42a from the first side of the aerosol carrier 14 flows across the activation surface 38 via the one or more channels 40 formed between the activation surface 38 and the conduction element 36 (or between the activation surface 38 and heater 24). Likewise, when the incoming air stream 42b from the second side of the aerosol carrier 14 reaches the second side of the activation surface 38, the incoming air stream 42b from the second side of the aerosol carrier 14 flows across the activation surface 38 via the one or more channels 40 formed between the activation surface 38 and the conduction element 36 (or between the activation surface 38 and heater 24). The air streams 44a and 44b from each side flowing through the one or more channels 40 are denoted by dashed lines in FIG. 12. As air streams 44a and 44b flow through the one or more channels 40, aerosol precursor in the activation surface 38, across which the air streams 44a and 44b flow, is released from the activation surface 38 by heat conveyed to the activation surface from the heater 24. Aerosol precursor released from the activation surface 38 is entrained in air streams 44a and 44b flowing through the one or more channels 40. In use, the heater 24 of the apparatus 12 conveys heat to the activation surface 38 of the fluid-transfer article 34 to raise a temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article 34. As the air streams 44a and 44b continue their passages in the one or more channels 40, more released aerosol precursor is entrained within the air streams 44a and 44b. When the air streams 44a and 44b entrained with aerosol precursor meet at a mouth of the outlet fluid communication pathway 48, they enter the outlet fluid communication pathway 48 and continue until they pass through filter element 52 and exit outlet fluid communication pathway 48, either as a single outgoing air stream, or as separate outgoing air streams 46 (as shown). The outgoing air streams 46 are directed to an outlet, from where it can be inhaled by the user directly (if the second end 18 of the aerosol capsule 14 is configured as a mouthpiece), or via a mouthpiece. The outgoing air streams 46 entrained with aerosol precursor are directed to the outlet (e.g. via a gas communication pathway within the housing of the carrier).

When the user initially draws on a mouthpiece of the apparatus (or one the second end 18 of the aerosol carrier 14, if configured as a mouthpiece), this will cause an air column located in the outlet fluid communication pathway 48 to move towards the outlet. In turn, this will draw air into the fluid communication pathway from the one or more channels 40. This will cause a pressure drop in the channels 40. To equalise the pressure in the channels 40, air will be drawn into the aerosol carrier 14, and thus into the channels 40 via the inlet apertures 50. During the period of lower pressure in the one or more channels 40 when the user begins to draw, aerosol precursor in the fluid-transfer medium will be released into the channels from the activation surface 38, because the aerosol precursor is drawn into the one or more channels by way of the lower pressure. This effect is in addition to the effect of releasing the aerosol precursor from the activation surface 38 by way of heat conveyed from the heater. The drawing of the aerosol precursor from the activation surface 38 by way of the user sucking on the mouthpiece of the apparatus (or one the second end 18 of the aerosol carrier 14, if configured as a mouthpiece) may produce a dragging effect on the volumetric rate of flow experienced by the user during a suction action, i.e. the user may have to suck harder to achieve a same volumetric rate of flow. This effect may manifest itself as a similar physical sensation experienced by the user as those experienced from a traditional smoking or tobacco product.

Figure 13:
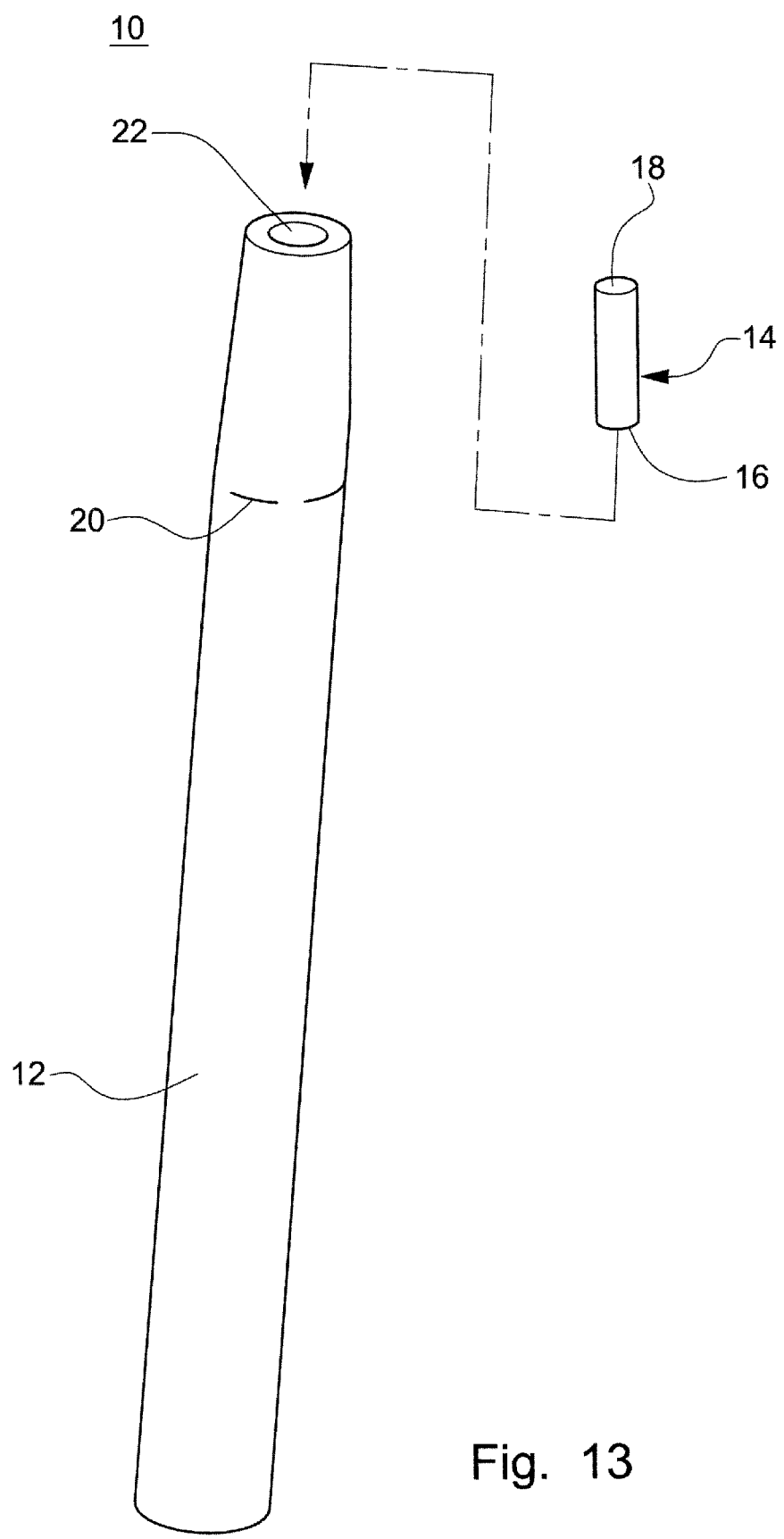
FIG. 13 is an exploded perspective view illustration of a kit-of-parts for assembling a system according to one or more embodiments of the present invention.

FIG. 13 is an exploded perspective view illustration of a kit-of-parts for assembling an aerosol delivery system 10.

As will be appreciated, in the arrangements described above, the fluid-transfer article 34 is provided within a housing 32 of the aerosol carrier 14. In such arrangements, the housing of the aerosol carrier 14 serves to protect the fluid-transfer article 34, whilst also allowing the aerosol carrier 14 to be handled by a user without his/her fingers coming into contact with the aerosol precursor liquid retained therein. In such arrangements, it will be appreciated that the aerosol carrier 14 has a multi-part construction. In some cases this might be considered somewhat disadvantageous because it requires a relatively complicated assembly procedure which can be both time-consuming and expensive. Turning now to consider FIG. 14, there is illustrated another possible aspect of the fluid-transfer article 34, which may be employed in some arrangements, and which may permit the creation of a significantly simplified aerosol carrier 14.

Figure 14:
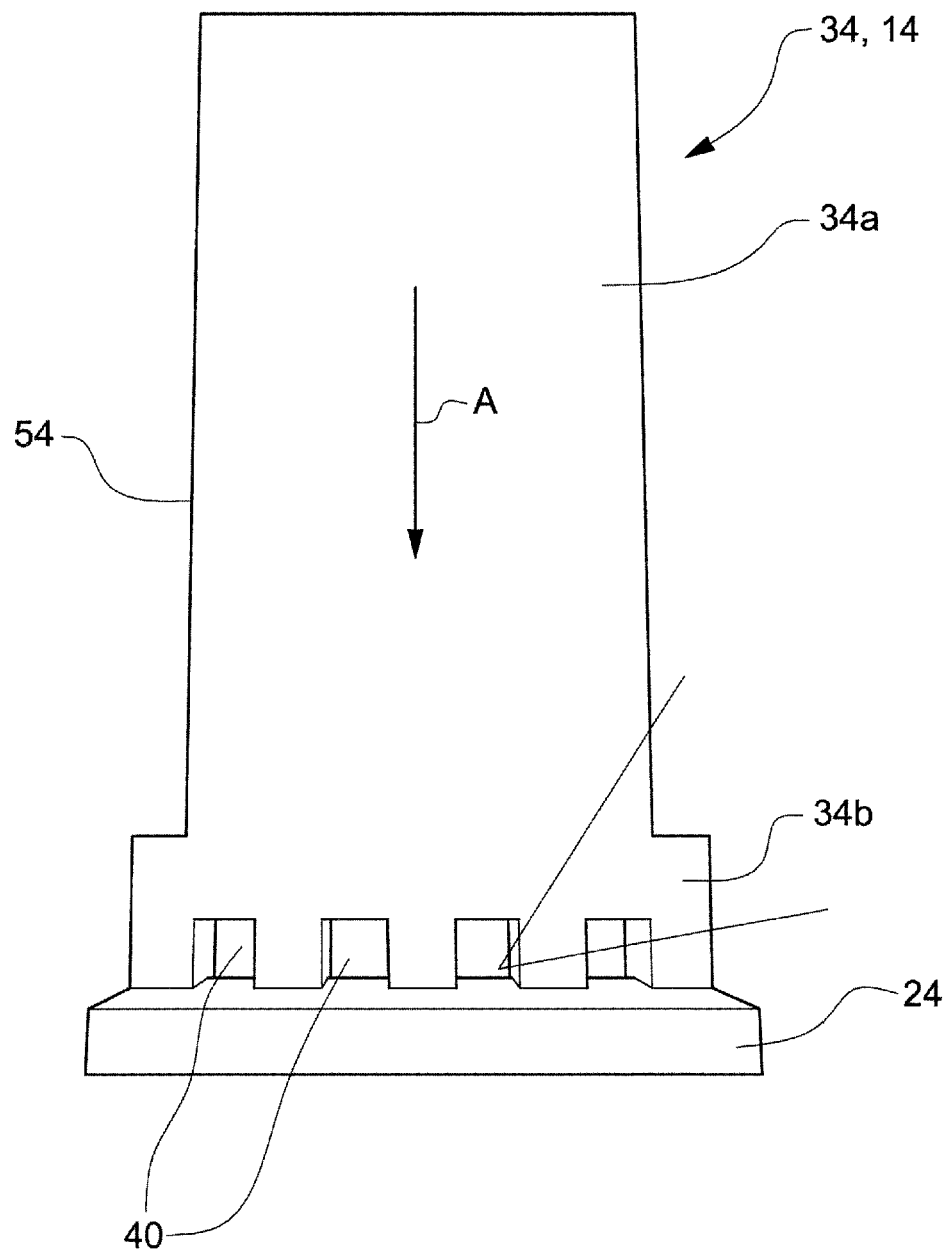
FIG. 14 is a cross-section side view of elements of an aerosol carrier and of part of an apparatus of the system for aerosol delivery according to one or more embodiments of the present invention.

FIG. 14 illustrates an alternative fluid-transfer article 34 in position adjacent a planar heater 24, such that the air flow channels 40 are positioned between the activation surface 38 and the heater 24. In the arrangement of FIG. 14, the substrate forming the fluid-transfer article 34 again comprises a porous material where pores of the porous material hold, contain, carry, or bear the aerosol precursor material. It is envisaged, for example, that the same types of substrate material may be used in the arrangement illustrated in FIG. 14 as in the previously-described arrangements. In particular, therefore, the porous material of the fluid-transfer article 34 may be a polymeric wicking material. However, in the arrangement illustrated in FIG. 14, the substrate material includes an integrally formed peripheral wall 54.

It is proposed that the peripheral wall 54 may be formed by treating the outermost surface of the porous substrate material of the fluid-transfer article 34 so as to render the surface substantially liquid-impermeable. For example, it is envisaged that in some arrangements the substrate material may be locally heated so as to fuse the material and close up its internal pores in the localised region of the surface. Alternatively, it is envisaged that the substrate material may be treated by a sintering process in order to create the liquid-impermeable peripheral wall 54. The peripheral wall 54 may alternatively be created by a chemical treatment process to render the substrate material substantially liquid-impermeable in the region of its outermost surface. As will therefore be appreciated, the peripheral wall 54 may be considered to take the form of a skin formed from the material of the substrate itself.

The peripheral wall may be created in this manner so as to substantially completely circumscribe the substrate material. It is to be appreciated, however, that the activation surface 38 of the fluid-transfer article 34 will not be treated in this manner, thereby ensuring that it will retain the function described above in detail in cooperation with the heater 24. The thickness of the peripheral wall 54 formed from the substrate may vary depending on the desired physical properties of the fluid-transfer article 34. For example, a relatively thin peripheral wall 54 might be desirable in some circumstances, as this may retain some flexibility in the material, thereby providing a fluid-transfer article which will feel soft in the hands of a user. Alternatively, a relatively thick peripheral wall 54 might be desirable in arrangements where the peripheral wall 54 is required to provide some structural rigidity to the fluid-transfer article 34. The peripheral wall 54 may therefore have a thickness of less than 3 mm; or less than 2.5 mm; or less than 2 mm; or less than 1.5 mm; or less than 1 mm; or less than 0.9 mm; or less than 0.8 mm; or less than 0.7 mm; or less than 0.6 mm; or less than 0.5 mm; or less than 0.4 mm; or less than 0.3 mm; or less than 0.2 mm; or less than 0.1 mm in some embodiments.

As will be appreciated, the liquid-impermeable nature of the resulting peripheral wall or skin means that the fluid-transfer article 34 may be handled by a user without getting his or her fingers wet from the aerosol precursor liquid retained therein. This opens up the possibility of the fluid-transfer article 34 being used without an enclosing housing 32, as was necessary in the previously-described arrangements. It is therefore envisaged that in some arrangements, the fluid-transfer article 34 may itself define an entire aerosol carrier 14. Furthermore, it is envisaged that in some embodiments, a fluid-transfer article 34 in accordance with this proposal may be provided in the form of a unitary monolithic element of substrate material and could, therefore, take the form of a single-piece consumable or aerosol carrier 14 for an aerosol-delivery system 10, which may be provided pre-filled with aerosol precursor liquid and which may be discarded when the initial volume of precursor has been used. A single-piece consumable of this type offers very significant advantages in terms of cost of manufacture, and from an environmental point of view.

Turning now to consider FIG. 15, there is illustrated a fluid-transfer article 34 in combination with a heater 24. The fluid-transfer article 34 may have a peripheral wall or skin formed in the manner described above, although this is not essential and indeed is not present in the particular arrangement illustrated in FIG. 15. The particular feature of the fluid-transfer article 34 illustrated in FIG. 15 which is of relevance is the cross-sectional profile of the channels 40 defined in the activation surface 38 of the second region 34*b* of the article. As will be noted, the channels 40 visible in FIG. 15 have a significantly different profile to the "saw-tooth" type profile illustrated in FIG. 5, and to the "castellated" type profile illustrated in FIG. 6. Nevertheless, as will be explained, the channel profile illustrated in FIG. 15 shares a characteristic with the "saw-tooth" type profile illustrated in FIG. 5.

The fluid-transfer article 34 is illustrated in FIG. 15 such that its activation surface 38 of the second region 34*b* is in direct engagement with a heating surface 55 of the heater 24. In the arrangement illustrated, the heater 24 may comprise a heater substrate defining a substantially planar heating surface, and may have a plurality of substantially parallel elongate heating elements 56 in the form of tracks or filaments formed on the heating surface 55, for example by printing or a convenient form of deposition. The heating elements 56 may comprise, for example, resistive heating filaments. They are arranged so as to extend generally parallel with the channels 40, with two such heating elements 56 being aligned with and located within each channel 40 when the fluid-transfer article 34 and the heater 24 are interengaged as illustrated.

The activation surface 38 of the arrangement of FIG. 15 is discontinuous in a manner such that it includes a plurality of spaced-apart angled surface portions 57, each of which is arranged to form an acute intersection angle 58 with the heating surface 55. The angled surface portions 57 of the activation surface 38 are arranged in pairs, the members of each pair cooperating to define opposing angled walls of a respective channel 40. In the particular channel configuration illustrated in FIG. 15, each channel 40 also comprises a respective ceiling portion 59 between the two spaced-apart angled surfaces 57. Each channel 40 further comprises a pair of opposed side walls 60, each of which interconnects an edge of a respective angled surface portion 57 and a respective side edge of the ceiling portion 59 (at an upper corner 61 of the channel 40).

In the arrangement illustrated in FIG. 15, the ceiling portion 59 of each channel 40 presents a substantially planar surface in spaced-relation to the heating surface 55. However, as will be explained below in relation to FIG. 6, in other arrangements the ceiling portion may alternatively present an arcuate surface towards the heating surface 55.

As will be observed, the "saw-tooth" channel profile illustrated in FIG. 5 can be considered somewhat similar to the profile illustrated in FIG. 15, in the sense that it is also defined by an activation surface 38 which is discontinuous in a manner effective to include angled surface portions arranged to form acute intersection angles with a planar heating surface. In the particular arrangement illustrated in FIG. 5, of course, the heating surface is defined by the conduction element 36 rather than the heater 24 itself.

It is believed that the aforementioned angled surfaces 57, and more particularly their acute intersection angles 58 to the heater surface 55 aid, in the release of liquid aerosol precursor from the substrate material of the fluid-transfer article 34. It is believed that the sharp corners defined at the angled points of intersection between the angled surfaces 57 and the heater surface 55 create improved vaporisation sites for the release of aerosol precursor, and allow the liquid to form menisci along the corner edges of the channels 40, at the sites of the acute angles 58, on the heating surface 55. This has been found to promote more efficient and quicker heating and vaporisation of the precursor liquid at the heating surface 55.

As will be observed, in the arrangement illustrated in FIG. 15, the heating elements 56 are arranged in relation to the channels 40 such that the pair of heating elements within each channel are offset from the centreline of the channel, to opposite sides. The heating elements are thus adjacent and proximate to the resulting corner edges of the channels 40 whilst nevertheless being spaced therefrom by a small distance. This allows the menisci of precursor liquid to form in the sharp corners of the channels immediately adjacent the heating elements 56 for improved heating and vaporisation.

The acute intersection angles 58 may all be substantially equal to one another, but this is not essential and indeed some embodiments are envisaged in which the acute intersection angles of the activation surface may be different to one another. Each intersection angle may be of any magnitude between 0 degrees and 90 degrees—i.e. greater than 0 degrees, and less than 90 degrees. Each intersection angle may be: greater than 10 degrees; greater than 20 degrees; greater than 30 degrees; greater than 40 degrees; greater than 50 degrees; greater than 60 degrees; greater than 70 degrees; greater than 80 degrees; less than 80 degrees; less than 70 degrees; less than 60 degrees; less than 50 degrees; less than 40 degrees; less than 30 degrees; less than 20 degrees; less than 10 degrees; and any combinations of the foregoing. The optimum intersection angle 58 for any given arrangement may depend on a number of factors such as, for example, the viscosity of the aerosol precursor liquid; the porosity of the substrate material of the fluid-transfer article 34; the particular material of the substrate; and/or the temperature achieved by the heater 24 at the heating surface 55.

Turning now to consider FIG. 16, there is illustrated a fluid-transfer article 34 having another configuration of activation surface 38. The fluid-transfer article 34 is illustrated as viewed from below the activation surface 38, and in the absence of a heater 24 or a conduction element 36 for the sake of clarity. Nevertheless, the notional operational position of the plane of the heating surface 55 which will be defined by the presence of the heater 24 or a conduction element 36 is illustrated in dashed lines for reference.

Figure 15:
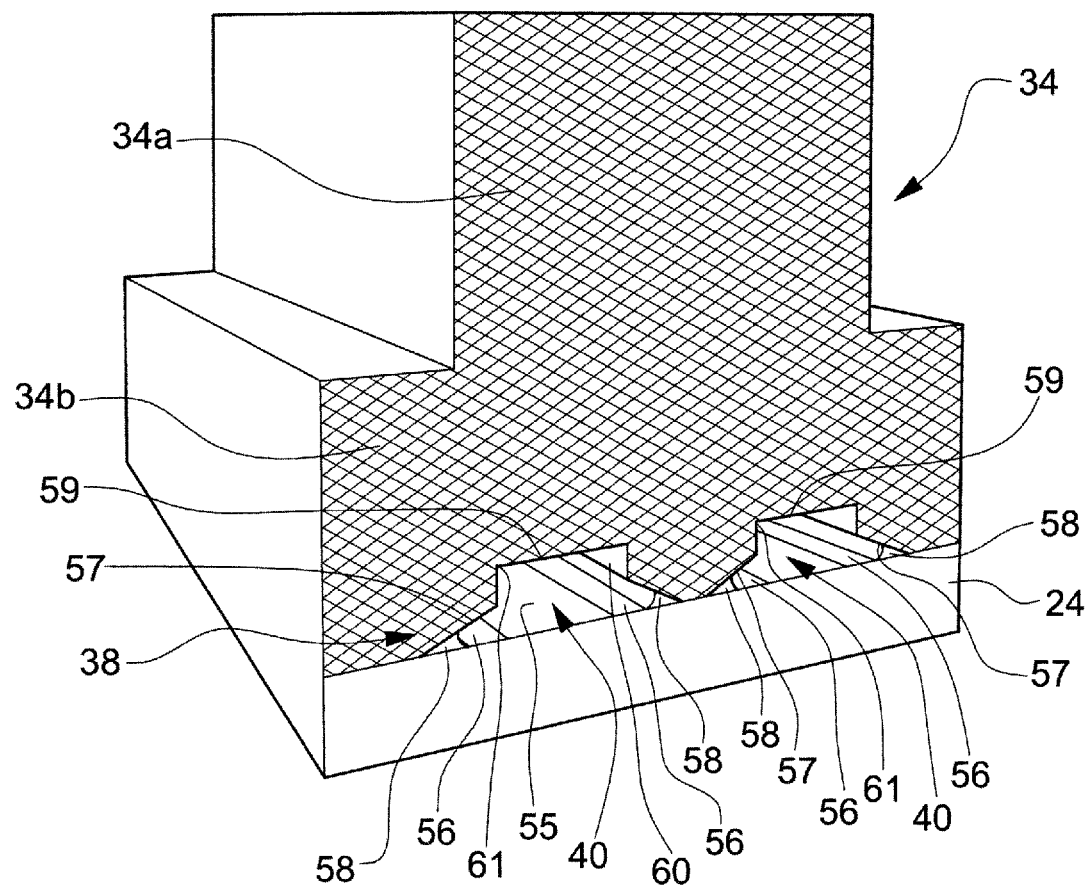
FIG. 15 is a cross-section view of elements of an aerosol carrier and of part of an apparatus of the system for aerosol delivery according to one or more embodiments of the present invention.
Figure 16:
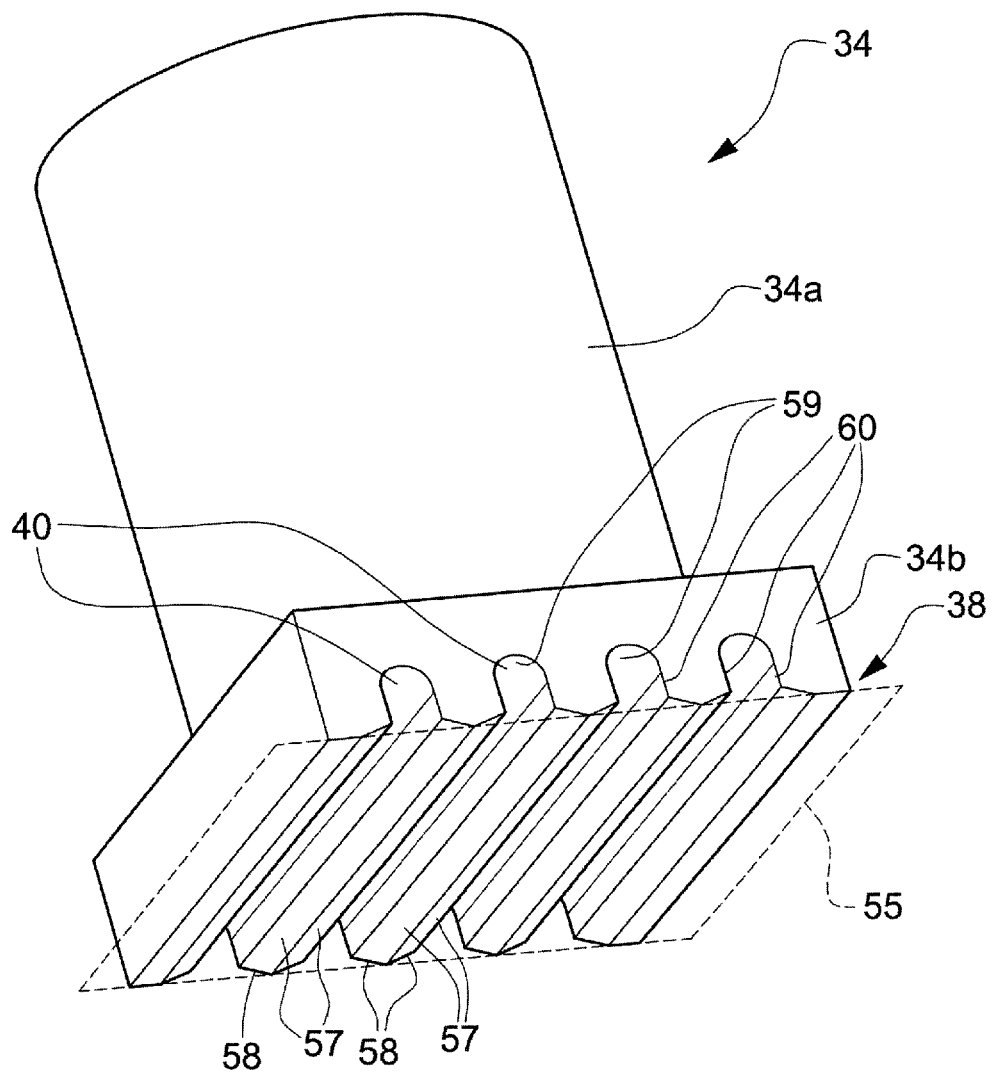
FIG. 16 is a perspective view of a fluid-transfer article of the system for aerosol delivery according to one or more embodiments of the present invention.
Figure 17:
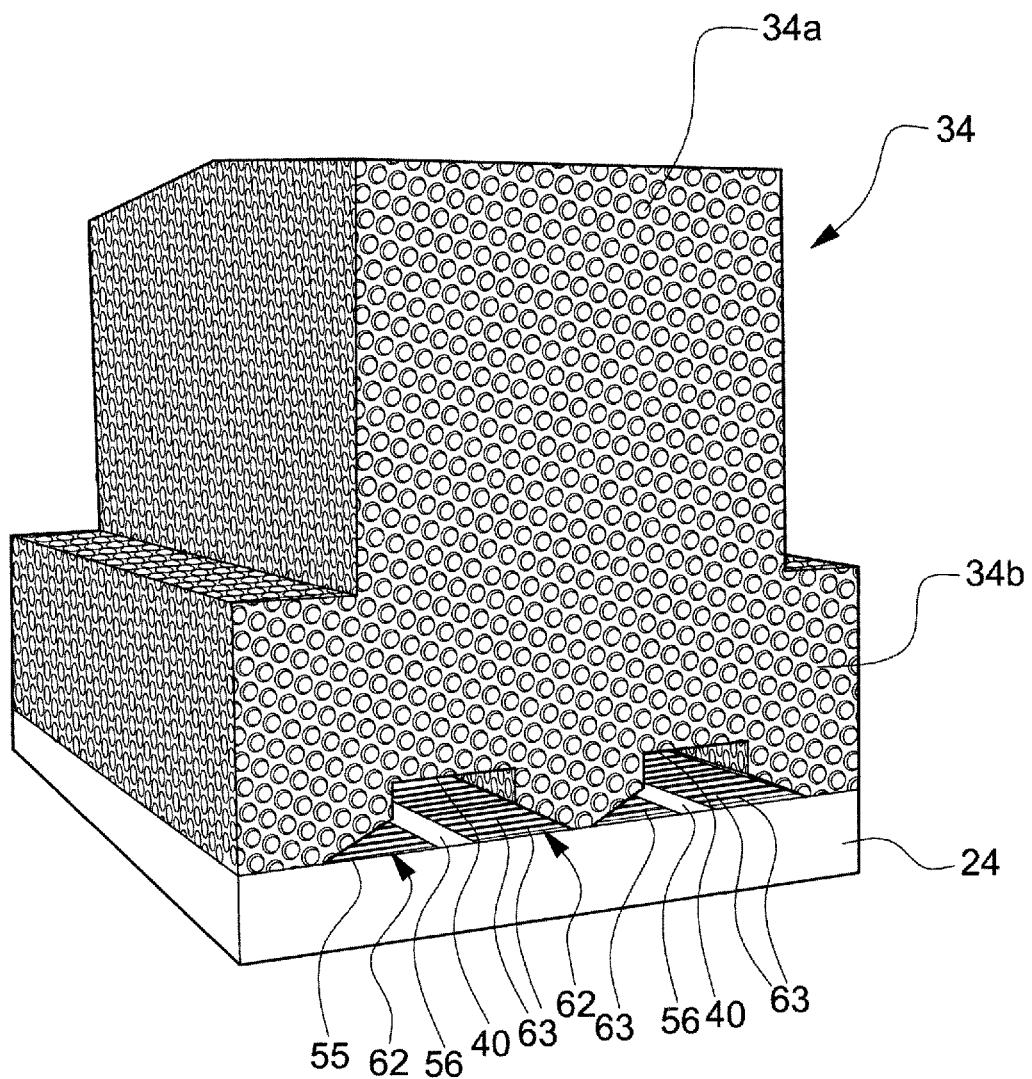
FIG. 17 is a cross-section view of elements of an aerosol carrier and of part of an apparatus of the system for aerosol delivery according to one or more embodiments of the present invention.

As will be observed from FIG. 16, the activation surface 38 is again discontinuous in a manner such that it includes a plurality of spaced-apart angled surface portions 57, each of which will form an acute intersection angle with the heating surface 55 when engaged thereagainst. In the particular arrangement illustrated, the intersection angles are considerably smaller than in the configuration illustrated in FIG. 15 and may, for example, be less than 20 degrees, although this is not essential.

Furthermore, it will also be observed that the angled surface portions 57 of the activation surface 38 are again arranged in pairs, the members of each pair cooperating to define opposing angled walls of a respective channel 40. In the particular channel configuration illustrated in FIG. 16, each channel 40 also comprises a respective pair of generally planar side walls 60 which are oriented so as to be substantially perpendicular to the plane of the heating surface 55 when the fluid-transfer article 34 and a heater 24 (or conduction element 36) are interengaged. The side walls 60 extend upwardly from the edges of respective angled surface portions 57, and are interconnected by a ceiling portion 59 of the respective channel 40. In this arrangement, the ceiling portion 59 of each channel 40 defines an arcuate surface portion, which it will be understood forms part of the discontinuous activation surface 38 of the fluid-transfer article. The arcuate surface portion of each channel 40 is arranged to oppose the heating surface 55, in spaced-relation thereto, and is concave towards the heating surface 55.

In preferred arrangements of the type illustrated in FIG. 16, it is proposed that the arcuate ceiling portion 59 of each channel will blend smoothly into the side walls 60 of the channel, thereby eliminating sharp corner edges in the upper region of the channel 40, distal to the heating surface 55. Such sharp corners can be seen, by comparison, in the arrangement of FIG. 15, and are denoted at 61. It has been found that by eliminating such sharp corners from the upper regions of the channels' cross-sectional profile, more efficient release or liberation of the aerosol precursor liquid from the porous substrate of the fluid-transfer article 34 may be achieved. This is because it has been found that liquid held in the wicking material has a tendency to collect at sharp corners of the channel profiles. Whilst this can be an advantage at the points where the activation surface 38 contacts the heating surface 55 (and may thus be promoted by the provision of the above-mentioned angled surface portions 57 and the resulting acute intersection angles 58), it can present a disadvantage at the top of each channel 40. This is because if excessive precursor liquid collects around the upper regions of the channel 40, it can be drawn out of the porous wicking material and carried away from the heating surface 55 by the airflow through the channel without having been heated and thus vaporised by contact with the heating surface.

In some arrangements, the or each channel 40 may be configured to have the above-described arrangement of spaced-apart side walls 60 and interconnecting arcuate ceiling portion 59 without the provision of the above-described angled surface portions 57, such that the lower edges of the side walls 60 will be configured for direct contact with the heating surface 55 of a heater 24 or conduction element 36.

FIG. 17 illustrates an arrangement which is similar in many respects to that illustrated in FIG. 15, but which incorporates an additional feature. As will be observed, whilst the arrangement illustrated in FIG. 15 is configured to include two elongate heating elements 56 within each air flow channel 40 of the fluid-transfer article 34, with each being located adjacent and proximate to the corner edges of the channel 40, in the arrangement of FIG. 17 there is only a single heating element 56 within each channel 40. As will also be noted, in the arrangement of FIG. 17, each heating element 56 is substantially aligned with the central longitudinal axis (centreline) of the respective channel 40. Noting that the heating elements 56 are thus spaced quite considerably from the corner edges of the air flow channels 40, where the porous substrate material of the fluid-transfer article 34 contacts the heater surface 55, it will therefore be appreciated that the heating elements 56 are spaced quite considerably from the positions at which the aerosol precursor liquid will most readily be drawn from the substrate material. In order to ensure that the precursor liquid is still properly heated and vaporised, the heater 24 thus includes an additional fluid transport feature to urge liquid across its heating surface 55 and towards the heating element 56, as will be described below.

The regions of the heating surface 55 adjacent each heating element are configured as fluid transport regions 62. There is thus a respective fluid transport region 62 on each side of each heating element 56, each fluid transport region 62 extending from a heating element 56 to (at least) a respective lower corner edge of the channel 40.

In the particular arrangement illustrated in FIG. 17, each fluid transport region 62 comprises a plurality of parallel capillary channels 63 which each take the form of an open-topped groove formed in the heating surface 55 of the heater 24. As will be noted, the capillary channels 63 each extend substantially perpendicular to the heating elements 56, from the heating elements 56 to (at least) the lower corner edges of each channel 40, where the substrate material meets the heating surface 55. It is to be appreciated, however, that in some embodiments the entire heating surface 55 may be provided with an array of capillary channels 63 which extend across its entire extent, and the heating elements 56 may then be formed across the capillary channels 63 so as to intersect them. In such an arrangement, the capillary channels 63 will also extend beneath the substrate material of the fluid-transfer article 34, between neighbouring air flow channels 40.

The capillary channels 63 serve to urge a flow of precursor liquid from the substrate material of the fluid-transfer article 34, across the heating surface 55 and towards the heating elements 56, by capillary action.

The fluid transport regions 62 of the heating surface 55 may, either as an alternative to the capillary channels 63 or in combination therewith, incorporate one or more other fluid transport features. For example, in some embodiments it is envisaged that the fluid transport regions 62 may comprise hydrophobic material to urge liquid across the regions. In some such arrangements, it is proposed that the hydrophobic material could be formed as a series of parallel elongate strips, in a similar pattern to that in which the capillary channels 63 are proposed. The capillary channels 63 themselves could be formed within a hydrophobic material.

In other embodiments, it is proposed to form the fluid transport regions 62 from porous material. For example, it is possible to configure the heater 24 so that it comprises a liquid-impermeable substrate supporting a porous and liquid-permeable fluid transport layer on top, such that the transport layer would then define the heating surface 55 on which the heating elements 56 may be provided. The porous transport layer may be formed from ceramic material.

Figure 18:
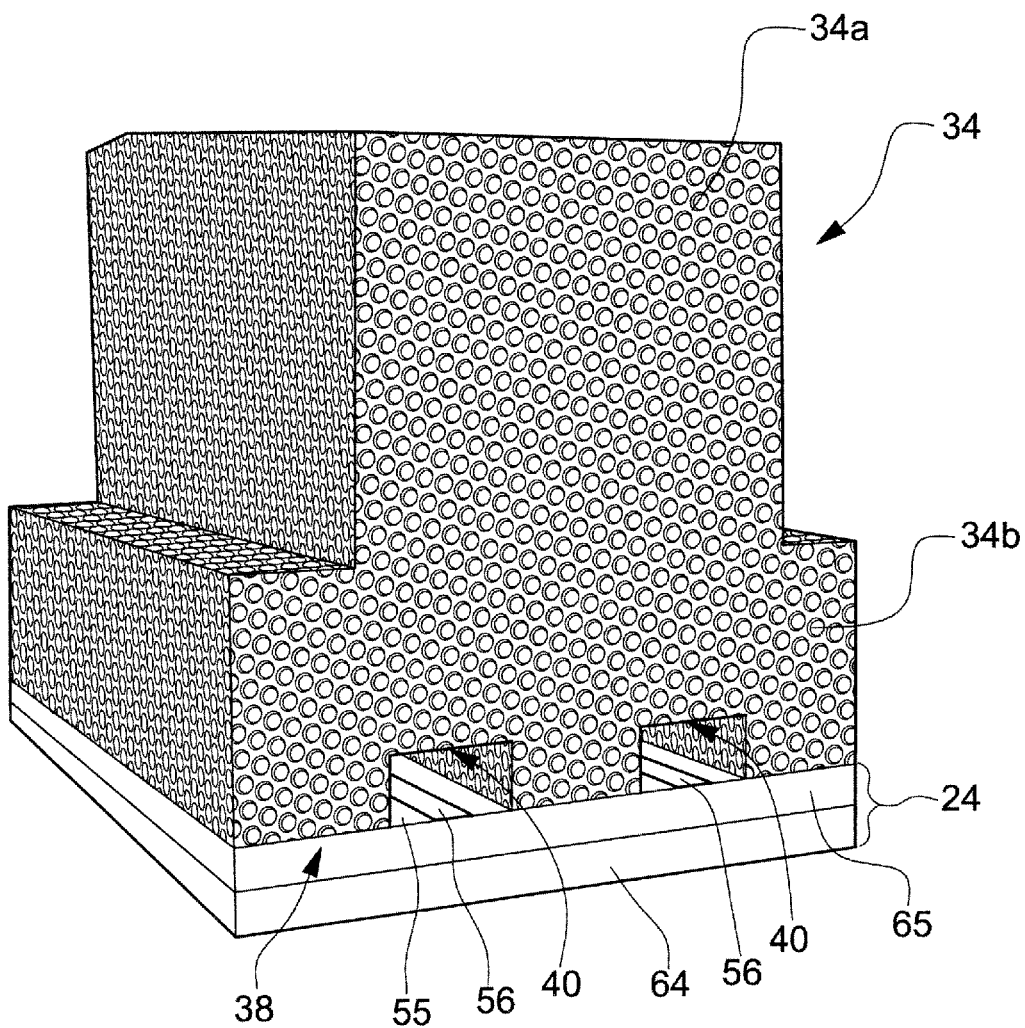
FIG. 18 is a cross-section view of elements of an aerosol carrier and of part of an apparatus of the system for aerosol delivery according to one or more embodiments of the present invention.

In FIG. 18, there is illustrated an arrangement in which the heater 24 has a laminate construction. More particularly, the heater 24 illustrated in FIG. 18 comprises a supporting substrate 64 which may be structural and which may be formed from a liquid-impermeable material such as, for example, metal, a non-porous ceramic, or a suitable hard plastics material. The supporting substrate 64 supports an overlying layer 65 of porous material such as, for example, a porous ceramic material. It is proposed that the porous material from which the overlying layer 65 is formed may be liquid-permeable. The overlying layer 65 of the heater defines the heating surface 55 of the heater, and the heating elements 56, which may again comprise resistive heating filaments, are laid directly on top of the porous layer, so as to be in contact therewith. The porous material of overlying layer 65 thus extends beneath the heating elements 56.

The porous layer may have a thickness of less than 5 mm. In other embodiments it may have a thickness of: less than 3.5 mm, less than 3 mm, less than 2.5 mm, less than 2 mm, less than 1.9 mm, less than 1.8 mm, less than 1.7 mm, less than 1.6 mm, less than 1.5 mm, less than 1.4 mm, less than 1.3 mm, less than 1.2 mm, less than 1.1 mm, less than 1 mm, less than 0.9 mm, less than 0.8 mm, less than 0.7 mm, less than 0.6 mm, less than 0.5 mm, less than 0.4 mm, less than 0.3 mm, less than 0.2 mm, or less than 0.1 mm.

As will be observed, when the fluid-transfer article 34 is engaged with the heater 24, the regions of the activation surface 38 which are located between the channels 40 make direct contact with the porous material of the overlying layer 65 of the heater. Furthermore, it will be noted that the heating elements 56 are located between the activation surface 38 (within the channels 40 thereof) and the porous material of the overlying layer 65. The overlying layer 65 thus serves to absorb aerosol precursor liquid from the second region 34b of the fluid-transfer article 34, via direct contact therewith, and thereafter to transfer the liquid towards the heating elements 56. As will be appreciated, because the heating elements 56 are formed directly on to the porous material, liquid within the porous material will be brought into contact with both the sides of the heating elements 56, at the heating surface 55, and also with the underside of the heating elements 56. The heating elements 56 are thus arranged for contact with a larger volume of precursor liquid, which has been found to improve the efficiency with which the liquid may be vaporised.

It is proposed that in some arrangements, the porous material of the heater 24 may be a porous wicking material, such as, for example, the materials identified above as candidates for the substrate forming the fluid-transfer article 34.

There has been described in the foregoing one or more proposals for an aerosol delivery system, and parts thereof, that avoids or at least ameliorates problems of the prior art.

In one or more optional arrangements, a fluid-transfer article 34 containing nicotine and/or nicotine compounds may be substituted or supplemented with a fluid-transfer article configured to provide a flavoured vapour and/or aerosol upon heating of the fluid-transfer article by the heater 24 of the apparatus 12. A precursor material for forming the flavoured vapour and/or aerosol upon heating is held within pores, spaces, channels and/or conduits within the fluid-transfer article. The precursor material may be extracted from a tobacco plant starting material using a supercritical fluid extraction process. Optionally, the precursor material is nicotine-free and comprises tobacco-flavours extracted from the tobacco plant starting material. Further optionally, the extracted nicotine-free precursor material (e.g. flavours only) could have nicotine added thereto prior to loading of the precursor material into the substrate of the carrier unit. Further optionally, flavours and physiologically active material may be extracted from plants other than tobacco plants.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

SEQUENCE LISTING

Not applicable.

The invention claimed is:

1. A fluid-transfer article comprising:

a first region for holding an aerosol precursor and for transferring said aerosol precursor to an activation surface of a second region of said article, said activation surface being disposed at an end of said article configured for thermal interaction with a heater of an aerosol-generation apparatus;

wherein at least said second region is formed from a polymeric wicking material, wherein said polymeric wicking material is porous, and is configured such that pore diameter in said first region is greater than pore diameter in said second region.

2. The fluid-transfer article according to claim 1, wherein said first and second regions are both formed from said polymeric wicking material.

3. The fluid-transfer article according to claim 2, wherein said polymeric wicking material is of greater hydrophilicity in said second region than said first region.

4. The fluid-transfer article according to claim 1, wherein said polymeric wicking material comprises at least one substance selected from the group consisting of: Polyetherimide (PEI); Polyether ether ketone (PEEK); Polytetrafluoroethylene (PTFE); Polyimide (PI); Polyethersulphone (PES); Ultra-High Molecular Weight Polyethylene (UHMWPE); Polypropylene (PP); and Polyethylene Terephthalate (PET).

5. The fluid-transfer article according to claim 1, wherein said polymeric wicking material is a hydrophilic material that is configured to transfer fluid from said first region to said second region.

6. The fluid-transfer article according to claim 1, wherein said polymeric wicking material comprises a graduated wicking action.

7. The fluid-transfer article according to claim 1, wherein said second region comprises at least one discontinuity in said activation surface to form a corresponding at least one channel between said activation surface and an opposing surface through which heat is conveyable to said activation surface from the heater, said at least one channel configured for providing a fluid pathway across said activation surface, said fluid pathway across said activation surface forming a portion of a fluid pathway between said first region and said second region.

8. A carrier for an aerosol precursor, the carrier comprising: the fluid-transfer article according to claim 1; and a housing for engagement with the aerosol-generation apparatus, said housing being configured to provide a fluid pathway between a first end that is disposed in fluid engagement with an inlet of said aerosol-generation apparatus and a second end that is disposed in fluid engagement with an outlet of said aerosol-generation apparatus; the fluid-transfer article being provided within said housing.

9. An aerosol-delivery system comprising: the carrier according to claim 8 and the aerosol-generation apparatus having the heater.

10. The fluid-transfer article of claim 1, further comprising:
- a liquid-impermeable peripheral wall surrounding at least a portion of said first region;
- wherein said first region comprises a storage substrate in which said aerosol precursor is held; and
- wherein said peripheral wall and said storage substrate are formed integrally from the same material as a one-piece unit.

11. The fluid-transfer article according to claim 10, wherein said storage substrate is porous, and said peripheral wall is non-porous.

12. The fluid-transfer article according to claim 10, wherein said peripheral wall is defined by a skin formed from the material of said storage substrate.

13. The fluid-transfer article according to claim 10, wherein said peripheral wall substantially completely circumscribes said storage substrate.

14. The fluid-transfer article according to claim 10, wherein at least said storage substrate is formed from porous material, an outermost surface of which has been treated to render the outermost surface liquid impermeable and thereby define said peripheral wall.

15. The fluid-transfer article according to claim 14, wherein said outermost surface has been treated by a process selected from the group consisting of comprising: heat-treatment, and chemical treatment.

16. The fluid-transfer article according to claim 10, the fluid-transfer article being provided in the form of a unitary monolithic element formed of said material, wherein said peripheral wall defines an outer surface of the fluid-transfer article across substantially the entire extent of said monolithic element, except said activation surface.

17. The fluid-transfer article according to claim 10, wherein said material is a second polymeric wicking material, wherein said second polymeric wicking material can be the same as said polymeric wicking material.

18. The fluid-transfer article according to claim 17, wherein said first and second regions are both formed from said polymeric wicking material.

19. The fluid-transfer article according to claim 10, wherein said material comprises a substance selected from the group consisting of: Polyetherimide (PEI); Polyether ether ketone (PEEK); Polytetrafluoroethylene (PTFE); Polyimide (PI); Polyethersulphone (PES); Ultra-High Molecular Weight Polyethylene (UHMWPE); Polypropylene (PP); and Polyethylene Terephthalate (PET).

20. The fluid-transfer article according to claim 10, wherein said material comprises Polyether ether ketone (PEEK).

21. The fluid-transfer article according to claim 10, wherein said material comprises Polytetrafluoroethylene (PTFE).

22. The fluid-transfer article according to claim 10, wherein said material comprises Polyimide (PI).

23. The fluid-transfer article according to claim 10, wherein said material comprises Polyethersulphone (PES).

24. The fluid-transfer article according to claim 10, wherein said material comprises Ultra-High Molecular Weight Polyethylene (UHMWPE).

25. The fluid-transfer article according to claim 10, wherein said material comprises Polypropylene (PP).

26. The fluid-transfer article according to claim 10, wherein said material comprises Polyethylene Terephthalate (PET).

27. The fluid-transfer article according to claim 10, wherein said second region comprises at least one discontinuity in said activation surface to form a corresponding at least one channel between said activation surface and an opposing surface through which heat is conveyable to said activation surface from the heater, said at least one channel configured for providing a fluid pathway across said activation surface, said fluid pathway across said activation surface forming a portion of a fluid pathway between said first region and said second region.

28. A carrier for an aerosol precursor, the carrier comprising a fluid-transfer article according to claim 10.

29. The carrier according to claim 28, the carrier being provided in the form of a consumable for an aerosol-delivery system, wherein said storage substrate contains a liquid aerosol precursor.

30. An aerosol-delivery system comprising: the carrier according to claim 28; and the aerosol-generation apparatus having the heater.

* * * * *